United States Patent
Wang et al.

(10) Patent No.: US 8,563,547 B2
(45) Date of Patent: Oct. 22, 2013

(54) (6,7-DIHYDRO-2-NITRO-5H-IMIDAZOL[2,1-B][1,3]OXAZIN-6-YL) AMIDE COMPOUNDS, PREPARATION METHODS AND USES THEREOF

(71) Applicants: Tiancai Wang, Pudong Shanghai (CN); Ting Xin, Pudong Shanghai (CN); Houxing Fan, Pudong Shanghai (CN); Yilang Chen, Pudong Shanghai (CN)

(72) Inventors: Tiancai Wang, Pudong Shanghai (CN); Ting Xin, Pudong Shanghai (CN); Houxing Fan, Pudong Shanghai (CN); Yilang Chen, Pudong Shanghai (CN)

(73) Assignee: Shanghai Sun-Sail Pharmaceutical Science & Technology Co., Ltd. (CN)

( * ) Notice: Subject to any disclaimer, the term of this patent is extended or adjusted under 35 U.S.C. 154(b) by 0 days.

(21) Appl. No.: 13/661,855

(22) Filed: Oct. 26, 2012

(65) Prior Publication Data
US 2013/0143864 A1 Jun. 6, 2013

Related U.S. Application Data

(63) Continuation of application No. PCT/CN2011/070734, filed on Jan. 28, 2011.

(30) Foreign Application Priority Data

Apr. 26, 2010 (CN) .......................... 2010 1 0155859

(51) Int. Cl.
*C07D 498/04* (2006.01)
*A61K 31/5365* (2006.01)

(52) U.S. Cl.
USPC ........................................ 514/230.2; 544/91

(58) Field of Classification Search
USPC .......................................... 544/91; 514/230.2
See application file for complete search history.

(56) References Cited

FOREIGN PATENT DOCUMENTS

| | | |
|---|---|---|
| CN | 101341150 A | 1/2009 |
| WO | 9701562 A1 | 1/1997 |

OTHER PUBLICATIONS

International Search Report Application No. PCT/CN2011/070734 Completed: Apr. 21, 2011; Mailing Date: May 26, 2011 5 Pages.
Li, et al.; "Synthesis and Antitubercular Activity of 7-(R)- and 7-(S)-methyl-2-nitro-6-(S)-(4-(trifluoromethoxy)benzyloxy)-6,7-dihydro-5H-imidazo[2,1-b][1,3]oxazines, analogues of PA-824"; Bioorg Med Chem Lett. Apr. 11, 2008; 4/(7): 2256-2262.
Sasaki, et al.; "Synthesis and antituberculosis activity of a novel series of optically active 6-nitro-2,3-dihydroimidazo[2,1-b]oxazoles"; Journal of Medicinal Chemistry [2006, 49(26):7854-7860] (1 page abstract).
Written Opinion of the International Searching Authority Application No. PCT/CN2011/070734 Completed: Apr. 27, 2011 5 pages.

*Primary Examiner* — Kahsay Habte
(74) *Attorney, Agent, or Firm* — St. Onge Steward Johnston & Reens LLC

(57) ABSTRACT

(6,7-Dihydro-2-nitro-5H-imidazo[2,1-b][1,3]oxazin-6-yl) amide compounds of formula (I), and their pharmaceutically acceptable salts, preparation methods and pharmaceutical compositions thereof are disclosed, wherein m and R are defined as in the description. The uses of the compounds in preparing medicaments for treating infectious diseases caused by *Mycobacterium tuberculosis*, especially infectious diseases caused by multi-drug resistance *Mycobacterium tuberculosi* are also disclosed.

9 Claims, 1 Drawing Sheet

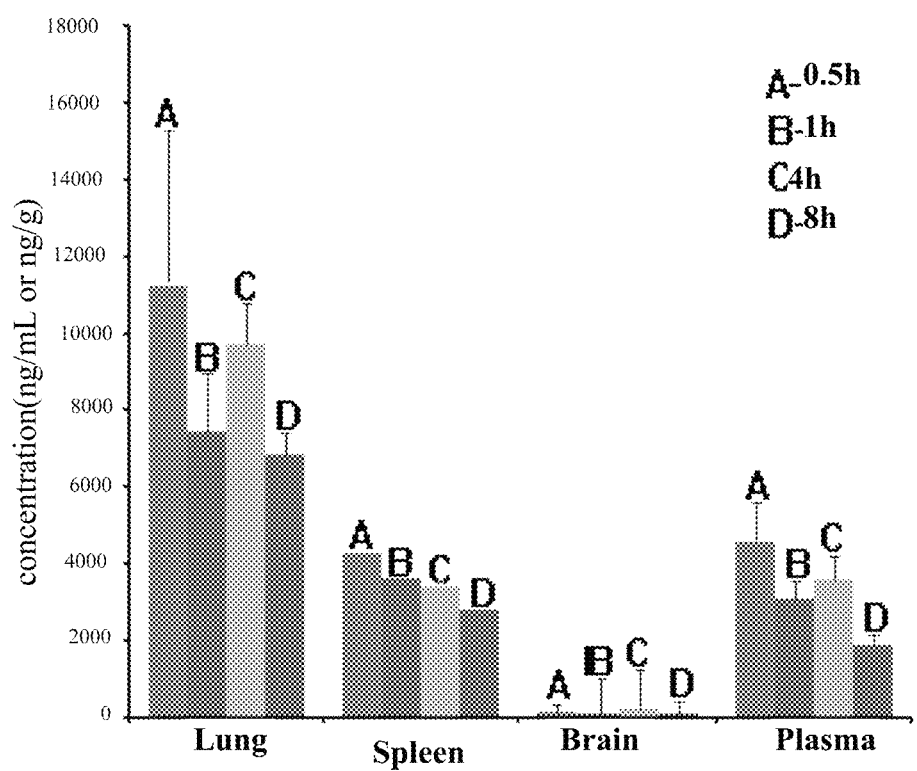

(6,7-DIHYDRO-2-NITRO-5H-IMIDAZOL [2,1-B][1,3]OXAZIN-6-YL) AMIDE COMPOUNDS, PREPARATION METHODS AND USES THEREOF

FIELD OF THE INVENTION

The present invention belongs to the field of pharmaceutics, relates to the fields of pharmaceutical chemistry and pharmacology, more particularly, relates to a new type of nitroimidazoles compound and preparation methods and uses thereof in medicaments for treating infectious diseases, especially infectious diseases caused by *Mycobacterium tuberculosis*.

BACKGROUND OF THE INVENTION

Tuberculosis, one of the oldest-known diseases, is caused by the infection of *Mycobacterium tuberculosis*, and even to this day is still seriously harmful to human health. According to the statistics of WHO, about ⅓ of people have been infected by *Mycobacterium tuberculosis* across the world, tuberculosis is an infectious disease which caused the largest number of deaths.

The current treatment of tuberculosis mainly uses the drug combination method of several first-line drugs such as isoniazide, rifampicin, ethambutol and pyrazinamide. This therapeutic method has the following disadvantages: long treatment cycle, often requires more than half a year; serious adverse reaction, eg., the drug combination of rifampicin and isoniazide is possible to cause serious liver disease, ethambutol can cause nerve injury; poor effect for drug resistance *Mycobacterium tuberculosi*, especially for multi-drug resistance *Mycobacterium tuberculosi*(MDR-TB), even ineffective.

WO9701562 disclosed a type of nitroimidazoles compound, particularly PA-824, which has a novel mechanism of action and can be used to treat tuberculosis. However, due to its low water-solubility and low bioavailability, PA-824 needs to be formulated into complex tablet formulation when administrated orally, and needs to further enhance its antitubercular activity [Bioorg. Med. Chem. Lett, 2008, 18(7), 2256-2262.].

Otsuka Pharmaceutical Co., Ltd also synthesized many nitroimidazoles compounds, particularly OPC-67683 [Journal of Medicinal Chemistry 2006, 49(26), 7854-7860], which acts similarly to PA-824 and is used to treat tuberculosis, but has the same problems as PA-824, especially water-solubility that limits its pharmacokinetics characters, and can be further improved.

In view of the above, there exists an urgent need to develop a novel antituberculosis drug in the art. This novel drug should have the following characteristics: effective for drug-resistance bacteria, especially multi-drug resistance bacteria; can be used combined with currently used first-line antituberculosis drugs; has ideal metabolic property, can be administrated orally.

SUMMARY OF THE INVENTION

The object of the present invention is to provide a type of novel drug which has good antitubercular activity and is suitable for oral administration, preparation methods and uses thereof.

In the first aspect of the present invention, a novel antituberculosis compound which has the structure of formula (I), or optical isomers, pharmaceutically acceptable salts (inorganic or organic salts), hydrates or solvates thereof are provided;

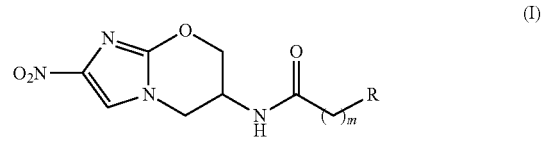

wherein, m refers to an integer between 1 and 4, R represents the following groups:

a). groups of the following structural formula

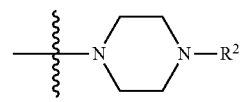

wherein, $R^2$ represents aryl methylene, which is unsubstituted or substituted by one to three groups independently selected from the following groups: halogen, halogen-substituted or unsubstituted $C_1$-$C_6$ alkoxy, halogen-substituted or unsubstituted $C_3$-$C_7$ cycloalkylalkoxy, wherein the above-mentioned alkoxy groups are selected from the following alkoxy groups: $OCH_3$, $OCF_3$, $CHF_2O$, $CF_3CH_2O$, $^iPrO$, $^nPrO$, $^iBuO$, $^cPrO$, $^nBuO$, or $^tBuO$;

b). or groups of the following structural formula

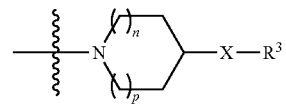

wherein, n and p represents an integer between 0 and 2 respectively, X refers to O, NH, $OCH_2$, $CH_2$ or chemical bonds, $R^3$ represents aryl, which is unsubstituted or substituted by one to three groups independently selected from the following groups: halogen, halogen-substituted or unsubstituted $C_1$-$C_6$ alkyl, halogen-substituted or unsubstituted $C_1$-$C_6$ alkoxy, halogen-substituted or unsubstituted $C_3$-$C_7$ cycloalkylalkoxy, halogen-substituted or unsubstituted alkoxy alkoxy, wherein the above-mentioned alkoxy groups are selected from the following alkoxy groups: $OCH_3$, $OCF_3$, $CHF_2O$, $CF_3CH_2O$, $MeOCH_2CH_2O$, $C_2H_5OCH_2CH_2O$, $CF_3CH_2OCH_2CH_2O$, $^iPrO$, $^nPrO$, $^iBuO$, $^cPrO$, $^nBuO$, or $^tBuO$;

For clarity, in $R^2$ and $R^3$ as described as above, $^iPrO$ refers to isopropoxy group, also conventionally written as iso-PrO; $^nPrO$ refers to normal proproxy group, also conventionally written as PrO; $^cPrO$ refers to cyclopropoxy group, also conventionally written as cyclo-PrO; $^iBuO$ refers to isobutoxy group, also conventionally written as iso-BuO; $^nBuO$ refers to normal butoxy group, also conventionally written as BuO; and $^tBuO$ refers to tertiary butoxy group, also conventionally written as tert-BuO.

c). or groups of the following structural formula

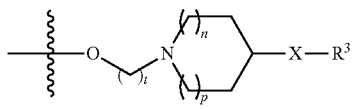

wherein, t refers to an integer between 2 and 5, n, p, X and $R^3$ are described as above.

In another preferred example, said $R^2$ refers to substituted or unsubstituted benzyl, preferably p-trifluoromethoxybenzyl, p-methylbenzyl, 4-(isopropoxy)benzyl or 4-(difluoromethoxy)benzyl.

In another preferred example, said $R^3$ refers to substituted or unsubstituted phenyl, preferably p-trifluoromethoxyphenyl, 2-fluoro-4-(trifluoromethoxy)phenyl, 3-fluoro-4-(trifluoromethoxy)phenyl, 3-fluoro-4-(trifluoromethoxy)phenyl, 3-fluoro-4-(trifluoromethyl)phenyl, 3,5-difluoro-4-(trifluoromethoxy)phenyl, 4-(2,2,2-trifluoroethoxy)phenyl, 4-(difluoromethoxy)phenyl, 4-(2-methoxyethoxy)phenyl, 4-(2-ethoxyethoxy)phenyl, 4-(2-(2,2,2-trifluoroethoxy)ethoxy)phenyl, 4-isopropoxyphenyl, 4-isobutoxyphenyl or 4-(2-(cyclopropoxy)ethoxy)phenyl.

In another preferred example, said compound of formula (I) selects from compound 1 to 26.

In the second aspect of the present invention, a pharmaceutical composition is provided, which comprises pharmaceutically acceptable excipients or carriers and the compound of formula (I) as the active ingredient of the present invention, or each optical isomers, pharmaceutically acceptable salts (including inorganic or organic salts), hydrates or solvates thereof.

In another preferred example, said composition is of oral dosage

In another preferred example, said oral dosage form is tablet, capsule, granule.

In the third aspect of the present invention, it provides the uses of a compound of formula (I) of the present invention, or each optical isomers, each crystal form, pharmaceutically acceptable salts, hydrates or solvates thereof. They are used to produce compositions which suppress the growth of *Mycobacterium tuberculosi*.

In the fourth aspect of the present invention, it provides the uses of a compound of formula (I) of the present invention, or each optical isomers, each crystal form, pharmaceutically acceptable salts, hydrates or solvates thereof. They are used to produce drugs which prevent or treat infection.

In another preferred example, said infection is pulmonary tuberculosis infection.

In another preferred example, said drug is used to suppress infections caused by *Mycobacterium tuberculosis*, especially infectious diseases caused by drug resistant *Mycobacterium tuberculosi* or multi-drug resistant *Mycobacterium tuberculosi*.

In the fifth aspect of the present invention, the preparation methods of a compound of formula (I), or each optical isomers, pharmaceutically acceptable inorganic or organic salts thereof are provided.

In another preferred example, it provides a preparation method of the compound of formula I-a, said method comprises steps as follows:

(a) React compound I-8 with the compound of formula II-b to produce the compound of formula I-a under the inert polar aprotic solvent and alkaline condition,

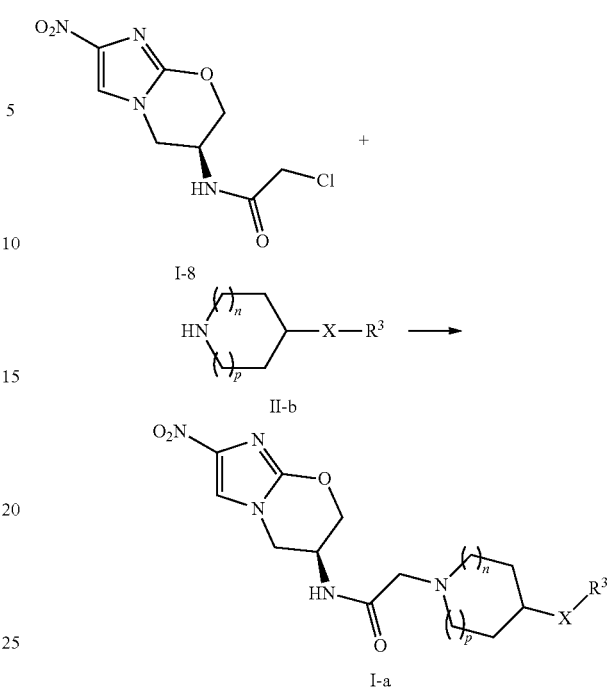

wherein, n and p represents an integer between 0 and 2 respectively,

X refers to O, NH, $OCH_2$, $CH_2$ or chemical bonds, $R^3$ represents aryl, which is unsubstituted or substituted by one to three groups independently selected from the following groups: halogen, halogen-substituted or unsubstituted $C_1$-$C_6$ alkyl, halogen-substituted or unsubstituted $C_1$-$C_6$ alkoxy, halogen-substituted or unsubstituted $C_3$-$C_7$ cycloalkylalkoxy, halogen-substituted or unsubstituted alkoxyalkoxy, wherein the above-mentioned alkoxy groups are selected from the following alkoxy groups: $OCH_3$, $OCF_3$, $CHF_2O$, $CF_3CH_2O$, $MeOCH_2CH_2O$, $C_2H_5OCH_2CH_2O$, $CF_3CH_2OCH_2CH_2O$, $^iPrO$, $^nPrO$, $^iBuO$, $^cPrO$, $^nBuO$, or $^tBuO$.

In another preferred example, said inert polar aprotic solvent is DMF; and said alkaline condition is in the presence of potassium carbonate.

In another preferred example, said method further comprises step (b): react the compound of formula I or I-a with acid, and form salts of said compound.

It will be understood that each above-mentioned technical feature of the present invention can combine with each technical feature described below (such as examples), thereby constituting new or preferred technical protocols. We don't describe more here owing to space reasons.

BRIEF DESCRIPTION OF THE DRAWINGS

FIG. 1 shows in one example of the present invention, the compound concentration (ng/mL (liquid sample) or ng/g (solid sample)) in embryo, lung, brain and plasma at different time after oral administration of mouse (25 mg/kg).

DETAILED DESCRIPTION OF THE INVENTION

The present inventors synthesized a large number of compounds by extensive structure-effect relationship investigations, and performed a lot of systematic research work such as in vitro screening, metabolism, tissue distribution, screening of drug-resistance *Mycobacterium tuberculosi*, discovered firstly that the compound of formula I had strong anti-Mycobacterium tuberculosi activity as well as good metabolic property and physicochemical property, particularly suitable for treating infectious diseases caused by *Mycobacterium tuberculosi*. The present inventor accomplished the present invention on this basis.

The name and structural formula of representative compounds (or their salts) in the compound of formula I of the present invention are shown in table 1 below:

TABLE 1

(I)

| compound structure | compound name |
| --- | --- |
| Compound 1 | (S)-N-(6,7-dihydro-2-nitro-5H-imidazo[2,1-b][1,3]oxazin-6-yl)-2-(4-(4-(trifluoromethoxy)phenoxy)piperid-1-yl)acetamide |
| Compound 2 | 2-(4-(2-fluoro-4-(trifluoromethoxy)phenoxy)piperid-1-yl)-N-((S)-6,7-dihydro-2-nitro-5H-imidazo[2,1-b][1,3]oxazin-6-yl)acetamide |
| Compound 3 | 2-(4-(3-fluoro-4-(trifluoromethoxy)phenoxy)piperid-1-yl)-N-((S)-6,7-dihydro-2-nitro-5H-imidazo[2,1-b][1,3]oxazin-6-yl)acetamide |
| Compound 4 | 2-(4-(3-chloro-4-(trifluoromethoxy)phenoxy)piperid-1-yl)-N-((S)-6,7-dihydro-2-nitro-5H-imidazo[2,1-b][1,3]oxazin-6-yl)acetamide |

TABLE 1-continued (I)

| | compound structure | compound name |
|---|---|---|
| Compound 5 | [structure] | 2-(4-(3-chloro-4-(trifluoromethyl)phenoxy)piperid-1-yl)-N-((S)-6,7-dihydro-2-nitro-5H-imidazo[2,1-b][1,3]oxazin-6-yl)acetamide |
| Compound 6 | [structure] | (S)-2-(4-(3,5-difluoro-4-(trifluoromethoxy)phenoxy)piperid-1-yl)-N-(2-nitro-6,7-dihydro-5H-imidazo[2,1-b][1,3]oxazin-6-yl)acetamide |
| Compound 7 | [structure] | (S)-N-(6,7-dihydro-2-nitro-5H-imidazo[2,1-b][1,3]oxazin-6-yl)-2-(4-(4-(trifluoromethoxy)phenoxy)piperid-1-yl)acetamide |
| Compound 8 | [structure] | 2-(3-(4-(trifluoromethoxy)phenoxy)azetidin-1-yl)-N-((S)-6,7-dihydro-2-nitro-5H-imidazo[2,1-b][1,3]oxazin-6-yl)acetamide maleate |
| Compound 9 | [structure] | (S)-2-(4-(4-(2,2,2-trifluoroethoxy)phenoxy)piperid-1-yl)-N-(2-nitro-6,7-dihydro-5H-imidazo[2,1-b][1,3]oxazin-6-yl)acetamide |

TABLE 1-continued (I)

| compound structure | compound name |
|---|---|
| Compound 10 | (S)-2-(4-(4-(difluoromethoxy)phenoxy)piperid-1-yl)-N-(2-nitro-6,7-dihydro-5H-imidazo[2,1-b][1,3]oxazin-6-yl)acetamide |
| Compound 11 | (S)-2-(4-(4-(2-methoxyethoxy)phenoxy)piperid-1-yl)-N-(2-nitro-6,7-dihydro-5H-imidazo[2,1-b][1,3]oxazin-6-yl)acetamide |
| Compound 12 | (S)-2-(4-(4-(2-ethoxyethoxy)phenoxy)piperid-1-yl)-N-(2-nitro-6,7-dihydro-5H-imidazo[2,1-b][1,3]oxazin-6-yl)acetamide |
| Compound 13 | (S)-2-(4-(4-(2-(2,2,2-trifluoroethoxy)ethoxy)phenoxy)piperid-1-yl)-N-(2-nitro-6,7-dihydro-5H-imidazo[2,1-b][1,3]oxazin-6-yl)acetamide |

TABLE 1-continued

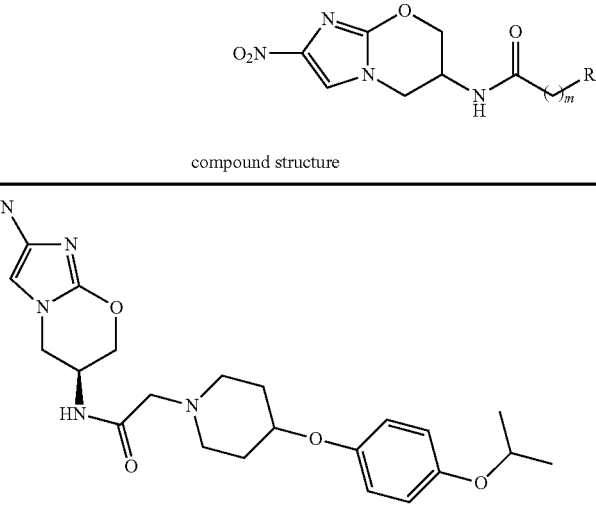

(I)

| compound structure | compound name |
|---|---|
| Compound 14 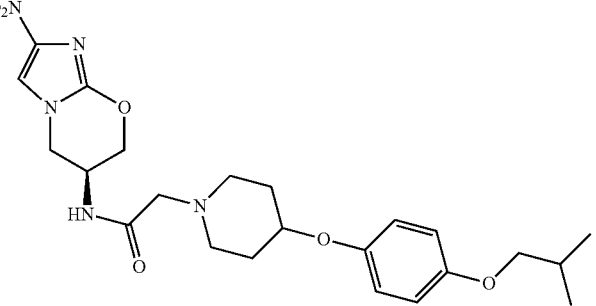 | (S)-2-(4-(4-isopropoxy)phenoxy)piperid-1-yl)-N-(2-nitro-6,7-dihydro-5H-imidazo[2,1-b][1,3]oxazin-6-yl)acetamide |
| Compound 15 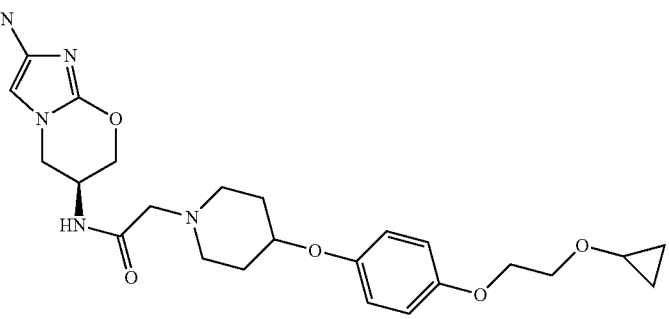 | (S)-2-(4-(4-isobutoxy)phenoxy)piperid-1-yl)-N-(2-nitro-6,7-dihydro-5H-imidazo[2,1-b][1,3]oxazin-6-yl)acetamide |
| Compound 16 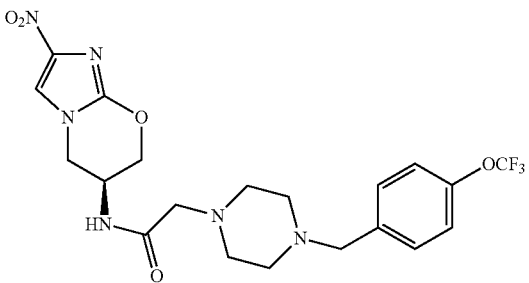 [SMILES: O=C(CN1CCN(Cc2ccc(OC(F)(F)F)cc2)CC1)N[C@@H]1COc2nc([N+](=O)[O-])cn2C1] | (S)-2-(4-(4-(2-(cyclopropoxy)ethoxy)phenoxy)piperid-1-yl)-N-(2-nitro-6,7-dihydro-5H-imidazo[2,1-b][1,3]oxazin-6-yl)acetamide |
| Compound 17 | (S)-N-(6,7-dihydro-2-nitro-5H-imidazo[2,1-b][1,3]oxazin-6-yl)-2-(4-(4-(trifluoromethoxy)benzyl)piperazin-1-yl)acetamide |

TABLE 1-continued (I)

| compound structure | compound name |
|---|---|
| Compound 18 | (S)-N-(2-nitro-6,7-dihydro-5H-imidazo[2,1-b][1,3]oxazin-6-yl)-2-(4-(4-(trifluoromethoxy)phenylamino)piperid-1-yl)acetamide |
| Compound 19 | (S)-N-(6,7-dihydro-2-nitro-5H-imidazo[2,1-b][1,3]oxazin-6-yl)-2-(4-(4-(trifluoromethoxy)phenyl)piperid-1-yl)acetamide |
| Compound 20 | 2-(4-(4-(trifluoromethoxy)benzyl)piperid-1-yl-N-((S)-6,7-dihydro-2-nitro-5H-imidazo[2,1-b][1,3]oxazin-6-yl)-acetamide |
| Compound 21 | 2-(2-(4-(4-(trifluoromethoxy)phenoxy)piperid-1-yl)ethoxy)-N-((S)-6,7-dihydro-2-nitro-5H-imidazo[2,1-b][1,3]oxazin-6-yl)acetamide |

TABLE 1-continued (I)

| compound structure | compound name |
|---|---|
| Compound 22 | (S)-N-(6,7-dihydro-2-nitro-5H-imidazo[2,1-b][1,3]oxazin-6-yl)-3-(4-(4-(trifluoromethoxy)phenoxy)piperid-1-yl)propanamide |
| Compound 23 | 3-(3-(4-(trifluoromethoxy)phenoxy)azetidin-1-yl)-N-((S)-6,7-dihydro-2-nitro-5H-imidazo[2,1-b][1,3]oxazin-6-yl)propanamide |
| Compound 24 | (S)-N-(6,7-dihydro-2-nitro-5H-imidazo[2,1-b][1,3]oxazin-6-yl)-3-(4-(4-(trifluoromethoxy)benzyl)piperazin-1-yl)propanamide |
| Compound 25 | 3-(2-(4-(4-(trifluoromethoxy)phenoxy)piperid-1-yl)ethoxy)-N-((S)-6,7-dihydro-2-nitro-5H-imidazo[2,1-b][1,3]oxazin-6-yl)propanamide |

TABLE 1-continued

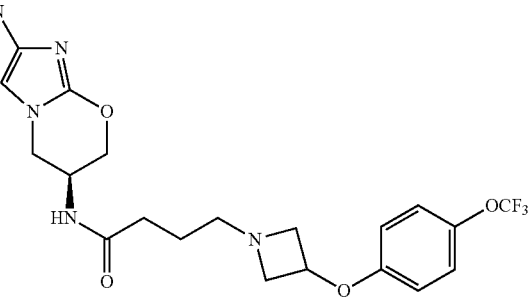

| | compound structure | compound name |
|---|---|---|
| Compound 26 | 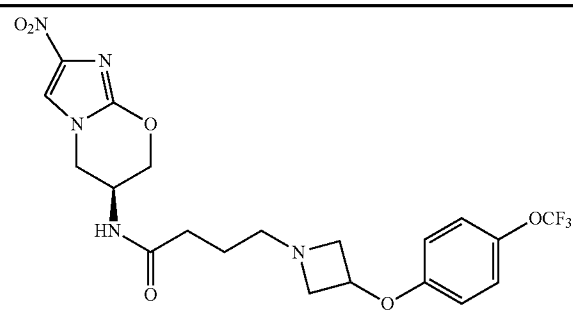 | 4-(3-(4-(trifluoromethoxy)phenoxy)azetidin-1-yl)-N-((S)-6,7-dihydro-2-nitro-5H-imidazo[2,1-b][1,3]oxazin-6-yl)butyramide |

Unless specifically stated, the following terms used in the specification and claims have the meanings as follows:

'Alkyl' refers to saturated aliphatic hydrocarbon groups, including straight-chain and branched-chain groups of 1 to 6 carbon atoms. Lower alkyl containing 1 to 4 carbon atoms are preferred, such as methyl, ethyl, propyl, 2-propyl, n-butyl, isobutyl, tert-butyl.

'Cycloalkyl' refers 3 to 7 membered full carbon monocyclic aliphatic hydrocarbon groups, wherein one or more rings can contain one or more double bonds, but none of them has full conjugated π-electronic system. For example, cyclopropyl, cyclobutyl, cyclopentyl, cyclohexane, cyclohexadiene, adamantane, cycloheptane, cycloheptatriene and the like. Cyclopropyl and cyclobutyl are more preferred.

'Alkoxy' refers to the alkyl bonded to the rest of the molecule through ether oxygen atom. Representative alkoxy is the alkyl of 1 to 6 carbon atoms, such as methoxy, ethoxy, propoxy, isopropoxy, butoxy, isobutoxy, sec-butoxy and tert-butoxy. As used herein, 'alkoxy' includes unsubstituted and substituted alkoxy, particularly alkoxy substituted by one or more halogens.

Preferred alkoxy groups are selected from: $OCH_3$, $OCF_3$, $CHF_2O$, $CF_3CH_2O$, $^iPrO$, $^nPrO$, $^iBuO$, $^cPrO$, $^nBuO$, or $^tBuO$.

'Aryl' refers to the group having at least one aromatic ring structure, ie, the aromatic ring which has conjugated π-electronic system, including carbocycloaryl, heteroaryl.

'Halogen' refers to fluorine, chlorine, bromine or iodine.

The compounds of the present invention can contain one or more asymmetric centers, and thus exist as the form of racemate, racemic mixture, individual enantiomer, diastereoisomer compound and individual diastereomer. The asymmetric centers which can exist are dependent on the properties of various substituents on molecule. Each of such asymmetric centers will independently produce two optical isomers, and all possible optical isomers and diastereomer mixture as well as pure or partically pure compounds are included in the scope of the invention. The present invention is intended to include all such isomeric forms of these compounds.

As used herein, 'pharmaceutically acceptable salts' means no limitation as long as salts are pharmaceutically acceptable, including inorganic or organic salts. Particularly, the salts formed by the compounds of the invention and acid can be listed, suitable salt-forming acids include (but not limited to) hydrochloric acid, hydrobromic acid, hydrofluoric acid, sulfuric acid, phosphoric acid, nitric acid, phosphoric acid and other inorganic acids, formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluenesulfonic acid and other organic acids as well as aspartic acid, glutamic acid and other acidic amino acids.

The Synthesis Method of the Compound of the Invention

The preparation methods of the structural compounds of formula (I) of the invention are particularly described below, but these particular methods construct no limitation to the present invention.

The structural compounds of formula (I) of the invention can be produced by the following method, however, the conditions of such method eg., reactant, solvent, base, the amount of used compounds, reaction temperature, time required by reaction and the like are not limited to the explanation below. The compounds of the invention are also optionally reaily produced by combing various synthesis methods described in the specification or known in the art. Such combination can be easily performed by the skill of the art belonging to the invention.

In the preparation methods of the invention, every reaction is often performed at the temperature from −30° C. to solvent's reflux temperature (preferably −20° C. to 80° C.) in inert solvent (generally polar aprotic solvent). Reaction time is usually 0.1 hr~60 hrs, more preferably 0.5 hr~48 hrs.

The preparation of the compounds of structural formula (I) are more particularly described below:

Process 1

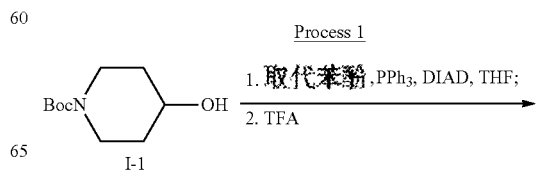

-continued

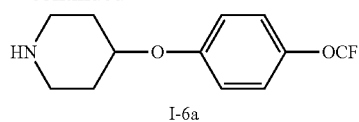
I-6a

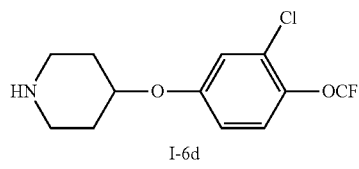
I-6d

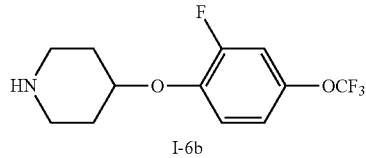
I-6b

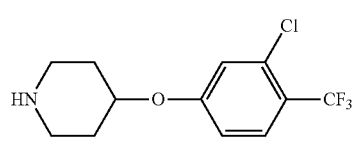
I-6e

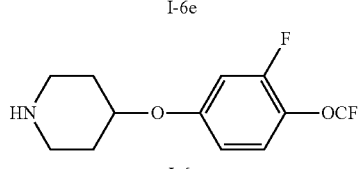
I-6c

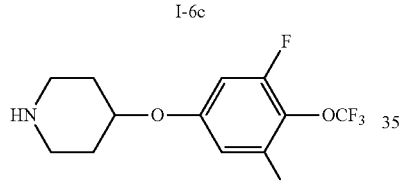
I-6f

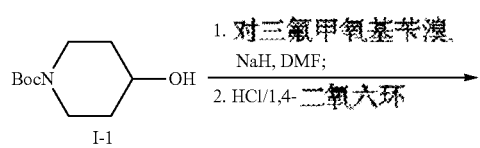
I-1 → 1. 对三氟甲氧基苄溴, NaH, DMF; 2. HCl/1,4-二氧六环

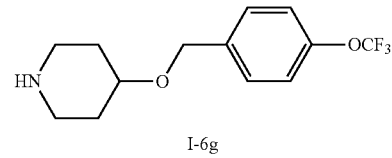
I-6g

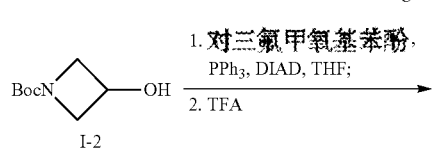
I-2 → 1. 对三氟甲氧基苯酚, PPh₃, DIAD, THF; 2. TFA

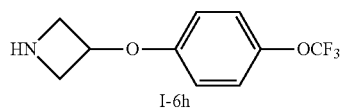
I-6h

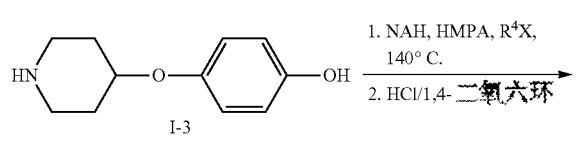
I-3 → 1. NaH, HMPA, R⁴X, 140° C.; 2. HCl/1,4-二氧六环

-continued

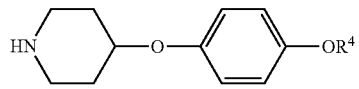

R⁴: I-6i: CF₃CH₂  I-6j: CF₂H  I-6k: CH₃OCH₂CH₂  I-6l: C₂H₅OCH₂CH₂
I-6m: CF₃CH₂OCH₂CH₂  I-6n: (CH₃)₂CH  I-6o: (CH₃)₂CHCH₂

I-6p: 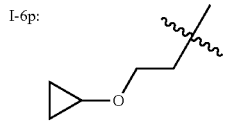

I-4 → 1. 对三氟甲氧基苄溴, NaI, K₂CO₃, THF; 2. TFA

I-6q

I-5 → 1. 对三氟甲氧基苯胺, NaBH(OAc)₃, DCM; 2. HCl/1,4-二氧六环

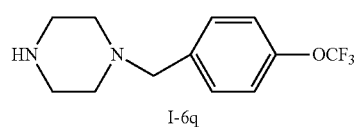
I-6r

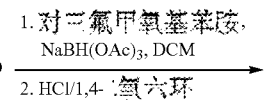
I-5 → 1.1 BuLi, 对三氟甲氧基溴苯; 1.2 Et₃SiH; 1.3 Pd/C; 2. HCl/1,4-二氧六环

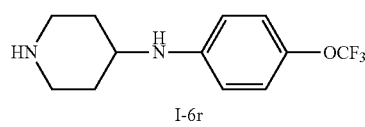
I-6s

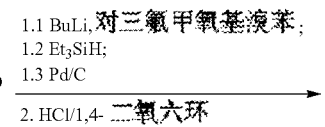
I-5 → 1.1 P(OEt)₃; 1.2 NaH, 对三氟甲氧基苄溴; 1.3 Pd/C; 2. HCl/1,4-二氧六环

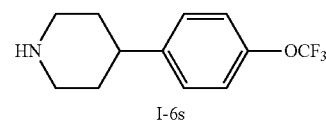
I-6t

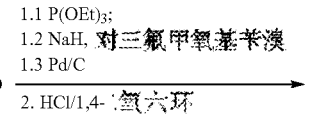
I-6a → (epoxide)/DCM

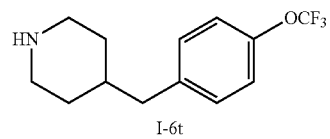

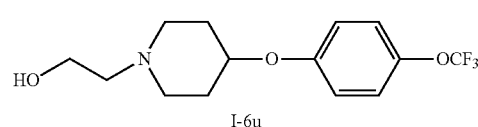
I-6u

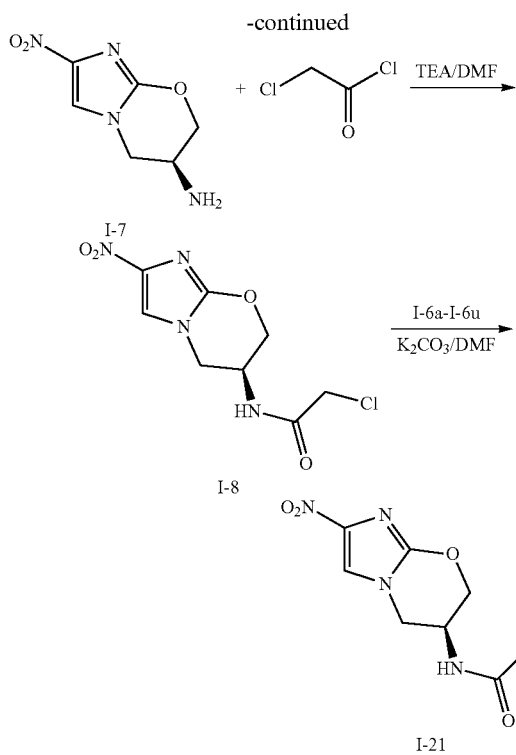

see table 1 for particular structures (1) Intermediate I-1 proceeded Mitsunobu reaction with various substituted phenols in the presence of triphenylphosphine and azo active ester, the resultant intermediate taked off Boc protecting group under acidic condition to give intermediate I-6a-I-6f. Tetrahydrofuran, 1,4-dioxane, methyl tert-butyl ether and the like can be choosed as solvents; azo active esters can be selected from DEAD, DIAD and the like. Optimum reaction conditions are to react 4-16 hours from −10° C. to room temperature in the presence of triphenylphosphine and DIAD, with tetrahydrofuran as solvent. Deprotected acids can be selected from (but not limited to) trifluoroacetic acid, hydrochloric acid and the like, solvents can be selected from (but not limited to) dichloromethane, 1,4-dioxane, tetrahydrofuran and the like, temperature is from −10° C. to room temperature. Optimum reaction conditions are to react with trifluoroacetic acid for 1-6 hours at room temperature.

(2) Intermediate I-1 reacts with p-trifluoromethoxy phenylhalide in polar aprotic solvent under alkaline condition, the resultant intermediate taked off Boc protecting group under acidic condition to give intermediate I-6a-I-6f. Bases can be selected from NaH, LiH, potassium tert-butoxide and the like, solvents can be selected from (but not limited to) DMF, acetonitrile, tetrahydrofuran and the like, optimum reaction conditions are to react with p-trifluoromethoxy bromobenzene for 2-24 hours at room temperature with NaH as base and DMF as solvent. Deprotected acids can be selected from (but not limited to) trifluoroacetic acid, hydrochloric acid and the like, solvents can be selected from dichloromethane, 1,4-dioxane, tetrahydrofuran and the like, temperature is from −10° C. to room temperature. Optimum reaction conditions are to directly react with hydrogen chloride-saturated 1,4-dioxane solution for 1-6 hours at room temperature.

(3) Intermediate I-2 proceeded Mitsunobu reaction with various substituted phenols in the presence of triphenylphosphine and azo active ester, the resultant intermediate taked off Boc protecting group under acidic condition to give intermediate I-6h. Solvents can be choosed from (but not limited to) tetrahydrofuran, 1,4-dioxane, methyl tert-butyl ether and the like; azo active esters can be selected from (but not limited to) DEAD, DIAD and the like. Optimum reaction conditions are to react 4-16 hours from −10° C. to room temperature in the presence of triphenylphosphine and DIAD, with tetrahydrofuran as solvent. Deprotected acids can be selected from (but not limited to) trifluoroacetic acid, hydrochloric acid and the like, solvents can be selected from (but not limited to) dichloromethane, 1,4-dioxane, tetrahydrofuran and the like, temperature is from −10° C. to room temperature. Optimum reaction conditions are to directly react with trifluoroacetic acid for 1-6 hours at room temperature.

(4) Intermediate I-3 reacts with various substituted agents with leaving groups in polar aprotic solvent under alkaline condition, the resultant intermediate taked off Boc protecting group under acidic condition to give intermediate I-6i-I-6p. Bases can be selected from (but not limited to) NaH, LiH, potassium tert-butoxide and the like, solvents can be selected from (but not limited to) HMPA, DMF, acetonitrile, tetrahydrofuran and the like, optimum reaction conditions are to react with various substituted agents with leaving groups for 6-24 hours at 80-200° C. with NaH as base and HMPA as solvent. Deprotected acids can be selected from (but not limited to) trifluoroacetic acid, hydrochloric acid and the like, solvents can be selected from (but not limited to) dichloromethane, 1,4-dioxane, tetrahydrofuran and the like, temperature is from −10° C. to room temperature. Optimum reaction conditions are to directly react with hydrogen chloride-saturated 1,4-dioxane solution for 1-6 hours at room temperature.

(5) Intermediate I-4 reacts with p-trifluoromethoxy phenylhalide in polar aprotic solvent under alkaline condition, the resultant intermediate taked off Boc protecting group under acidic condition to give intermediate I-6q. Bases can be selected from potassium carbonate, sodium carbonate, cesium carbonate, potassium tert-butoxide and the like, solvents can be selected from DMF, acetonitrile, tetrahydrofuran and the like, optimum reaction conditions are to react with p-trifluoromethoxy bromobenzene for 6-24 hours at room temperature with potassium carbonate as base, sodium iodide as catalyst and THF as solvent. Deprotected acids can be selected from (but not limited to) trifluoroacetic acid, hydrochloric acid and the like, solvents can be selected from (but not limited to) dichloromethane, 1,4-dioxane, tetrahydrofuran and the like, temperature is from −10° C. to room temperature. Optimum reaction conditions are to directly react with trifluoroacetic acid for 1-6 hours at room temperature.

(6) Crude material I-5 is a corresponding intermediate given by proceeding reductive amination with p-trifluoromethoxy for 1-24 hours in polar solvent in the presence of reducing agent. The latter one taked off Boc protecting group under acidic condition to give intermediate I-6r. Polar solvents can be selected from (but not limited to) methanol, ethanol, isopropanol, tetrahydrofuran, dichloromethane, 1,2-dichloroethane, 1,4-dioxane, DMF, acetonitrile, dimethoxyethane and the like. Reducing agents are selected from (but not limited to) sodium borohydride, potassium borohydride, cyano-sodium borohydride, sodium triacetoxyborohydride and the like. Optimum reaction conditions are to react for 4-24 hours at room temperature with dichloromethane as solvent and sodium triacetoxyborohydride as reducing agent. Deprotected acids can be selected from (but not limited to) trifluoroacetic acid, hydrochloric acid and the like, solvents can be selected from (but not limited to) dichloromethane, 1,4-dioxane, tetrahydrofuran and the like, temperature is from −10° C. to room temperature. Optimum reaction conditions are to directly react with hydrogen chloride-saturated 1,4-dioxane solution for 1-6 hours at room temperature.

(7) Crude material I-5 is a corresponding intermediate given by proceeding nucleophilic addition reaction with 4-trifluoromethoxy bromobenzene for 1-24 hours at −80° C. to 0° C. in polar aprotic solvent under the condition of lithium alkoxy. The latter one reduced under neutral or acidic condition, finally taked off Boc protecting group under acidic condition to give intermediate I-6s. Polar aprotic solvents can be selected from (but not limited to) tetrahydrofuran, 1,4-dioxane, dimethoxyethane and the like. Optimum reaction conditions are to react for 4-24 hours at room temperature with tetrahydrofuran as solvent and triethyl silicane as reducing agent. Deprotected acids can be selected from (but not limited to) trifluoroacetic acid, hydrochloric acid and the like, solvents can be selected from (but not limited to) dichloromethane, 1,4-dioxane, tetrahydrofuran and the like, temperature is from −10° C. to room temperature. Optimum reaction conditions are to directly react with hydrogen chloride-saturated 1,4-dioxane for 1-6 hours at room temperature.

(8) Crude material I-5 is a corresponding intermediate given by proceeding nucleophilic addition reaction with 4-trifluoromethoxy bromobenzene for 1-24 hours at −20° C. to 25° C. in polar aprotic solvent under the condition of lithium alkoxy in the presence of triethyl phosphate or triphenylphosphate. The latter one reduced under neutral condition, finally taked off Boc protecting group under acidic condition to give intermediate I-6t. Polar aprotic solvents can be selected from (but not limited to) tetrahydrofuran, dichloromethane, 1,2-dichloroethane, 1,4-dioxane, DMF, acetonitrile, dimethoxyethane and the like. Deprotected acids can be selected from (but not limited to) trifluoroacetic acid, hydrochloric acid and the like, solvents can be selected from (but not limited to) dichloromethane, 1,4-dioxane, tetrahydrofuran and the like, temperature is from −10° C. to room temperature. Optimum reaction conditions are to directly react with hydrogen chloride-saturated 1,4-dioxane solution for 1-6 hours at room temperature.

(9) Crude material I-6a reacts with excess ethylene oxide in polar aprotic solvent at −20° C. to room temperature to give intermediate I-6u. Polar aprotic solvents can be selected from (but not limited to) THF, dichloromethane, 1,2-dichloroethane, 1,4-dioxane, DMF, acetonitrile and the like. Optimum reaction conditions are to react with excess ethylene oxide for 1-6 hours at −10° C.-0° C. with dichloromethane as solvent.

(10) Intermediate I-7-(S)-2-nitro-6,7-dihydro-5H-imidazo[2,1-b][1,3]oxazine-6-amine) (Journal Medicinal Chemstry, 2009, 52(5), 1329-1344) reacts with chloroacetyl chloride or bromoacetyl chloride in polar aprotic solvent for 1-12 hours at −20-50° C. under alkaline condition to give intermediate I-8. Polar aprotic solvents can be selected from (but not limited to) DMF, NMP, THF, $CH_3CN$, DCM, $CHCl_3$, bases can be selected from (but not limited to) organic bases such as DIEA, TEA, DBU, pyridine, N-methylmorpholine and inorganic bases such as $K_2CO_3$, $Na_2CO_3$, $Cs_2CO_3$. Optimum reaction conditions are to react for 1-4 hours at −10° C.-10° C. with DMF as solvent and TEA as base.

(11) Intermediate I-8 reacts with I-6a-I-tu for 2-24 hours at −100° C. in polar aprotic solvent under alkaline condition to give compound I-21. Polar aprotic solvents can be selected from (but not limited to) DMF, NMP, THF, $CH_3CN$, DCM, $CHCl_3$, bases can be selected from (but not limited to) organic bases such as DIEA, TEA, DBU, pyridine, N-methylmorpholine and inorganic bases such as $K_2CO_3$, $Na_2CO_3$, $Cs_2CO_3$.

Optimum reaction conditions are to react for 6-16 hours at 20° C.-80° C. with DMF as solvent and $K_2CO_3$ as base.

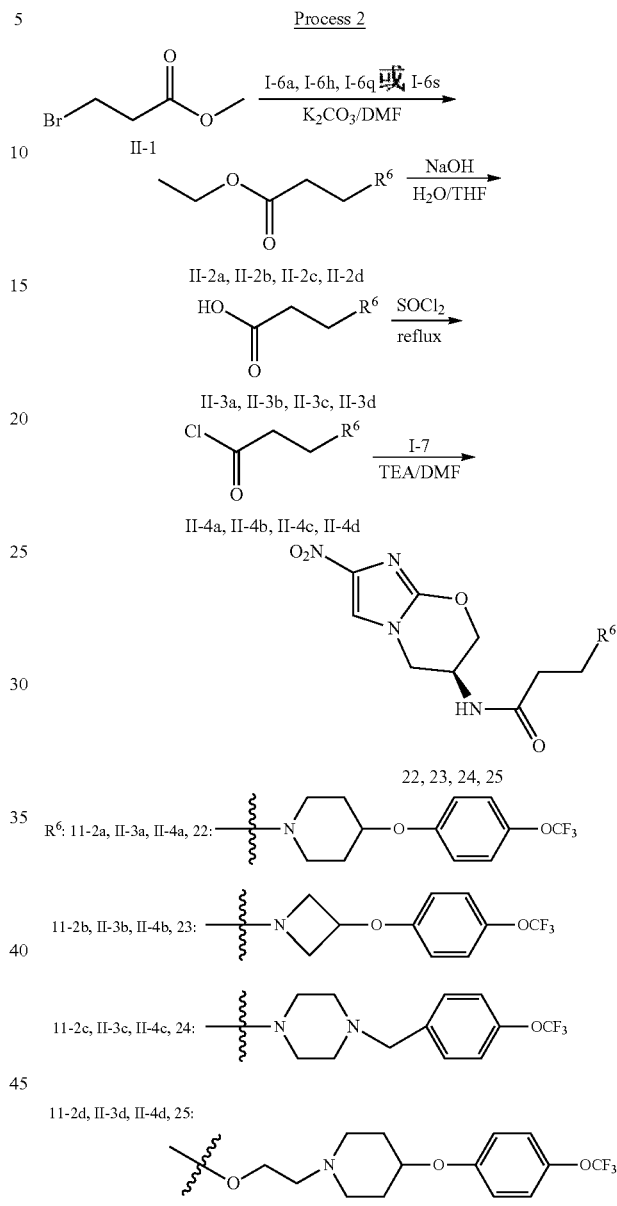

(1) 3-ethyl-bromopropionate in polar aprotic solvent reacts with various substituted amines or alcohols for 2-12 hours at room temperature-100° C. under alkaline condition to give intermediates II-2a, II-2b, II-2c and II-2d. Polar aprotic solvents can be selected from (but not limited to) DMF, NMP, THF, $CH_3CN$, DCM, $CHCl_3$, bases can be selected from (but not limited to) organic bases such as DIEA, TEA, DBU, pyridine, N-methylmorpholine and inorganic bases such as $K_2CO_3$, $Na_2CO_3$, $C_{S2}CO_3$. Optimum reaction conditions are to react for 1-6 hours at 50° C.-90° C. with $CH_3CN$ as solvent and $K_2CO_3$ as base.

(2) Intermediates II-2a, II-2b, II-2c and II-2d are hydrolyzed under alkaline condition to give intermediates II-3a, II-3b, II-3c and II-3d, bases can be selected from (but not limited to) inorganic bases such as NaOH, LiOH, KOH, $K_2CO_3$, solvents can be selected from (but not limited to)

MeOH, EtOH, THF, H₂O or one or more combinations of these. Optimum reaction conditions are to react for 2-6 hours at −10-30° C. with NaOH, H₂O and THF as mixed solvent.

(3) Intermediates II-3a, II-3b, II-3c and II-3d react with chlorination agent without solvent or in polar aprotic solvent to give intermediates II-4a, II-4b, II-4c and II-4d. Polar aprotic solvents can be selected from (but not limited to) THF, DCM, CHCl₃, PhCH₃ and the like, chlorination agents can be selected from (but not limited to) SOCl₂, (COCl)₂, POCl₃ and the like. Optimum reaction conditions are to reflux for 2-6 hours in SOCl₂ under the condition without solvent.

(4) Intermediates II-4a, II-4b, II-4c and II-4d in polar aprotic solvent react with intermediate I-7 for 1-12 hours at −20° C.-50° C. under alkaline condition to give product 22, 23, 24 and 25. Polar aprotic solvents can be selected from (but not limited to) DMF, NMP, THF, CH₃CN, DCM, CHCl₃, bases can be selected from (but not limited to) organic bases such as DIEA, TEA, DBU, pyridine, N-methylmorpholine and inorganic bases such as K₂CO₃, Na₂CO₃, CS₂CO₃. Optimum reaction conditions are to react for 2-12 hours at −10-50° C. with DMF as solvent and TEA as base.

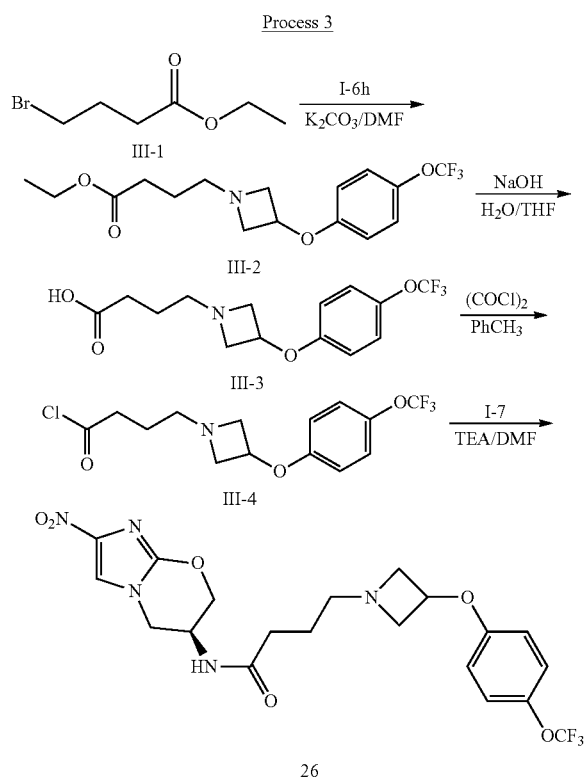

(1) 4-ethyl-bromobutyrate in polar aprotic solvent reacts with substituted amines for 2-12 hours at room temperature −100° C. under alkaline condition to give intermediate III-2. Polar aprotic solvents can be selected from (but not limited to) DMF, NMP, THF, CH₃CN, DCM, CHCl₃, bases can be selected from (but not limited to) organic bases such as DIEA, TEA, DBU, pyridine, N-methylmorpholine and inorganic bases such as K₂CO₃, Na₂CO₃, CS₂CO₃. Optimum reaction conditions are to react for 1-6 hours at 50-90° C. with CH₃CN as solvent and K₂CO₃ as base.

(2) Intermediate III-2 was hydrolyzed under alkaline condition to give intermediate III-3, bases can be selected from (but not limited to) inorganic bases such as NaOH, LiOH, KOH, K₂CO₃, solvents can be selected from (but not limited to) MeOH, EtOH, THF, H₂O or one or more combinations of these. Optimum reaction conditions are to react for 2-6 hours at −10-30° C. with NaOH, H₂O and THF as mixed solvent.

(3) Intermediate III-3 reacts with chlorination agent without solvent or in polar aprotic solvent to give intermediates III-4. Polar aprotic solvents can be selected from (but not limited to) THF, DCM, CHCl₃, PhCH₃ and the like, chlorination agents can be selected from (but not limited to) SOCl₂, (COCl)₂, POCl₃ and the like. Optimum reaction conditions are to reflux for 2-6 hours in SOCl₂ under the condition without solvent.

(4) Intermediate III-4 in polar aprotic solvent reacts with intermediate I-7 for 1-12 hours at −20° C.-50° C. under alkaline condition to give product 26. Polar aprotic solvents can be selected from (but not limited to) DMF, NMP, THF, CH₃CN, DCM, CHCl₃, bases can be selected from (but not limited to) organic bases such as DIEA, TEA, DBU, pyridine, N-methylmorpholine and inorganic bases such as K₂CO₃, Na₂CO₃, CS₂CO₃. Optimum reaction conditions are to react for 2-12 hours at −10-50° C. with DMF as solvent and TEA as base.

Pharmaceutical Compositions and Administration Methods

Since the compound of the present invention has superior antitubercular activity, the compound of the present invention and each crystal form, pharmaceutically acceptable inorganic or organic salts thereof, as well as pharmaceutical compositions containing the compound of the present invention as main active ingredient can be used to treat diseases associated with *Mycobacterium tuberculosis*. According to the current techniques, the compound of the present invention can be used to teat tuberculosis and other infectious diseases.

The pharmaceutical compositions of the present invention comprise safe and effective amount of the compound of the present invention or pharmaceutically acceptable salts and pharmaceutically acceptable excipients and carriers thereof. Wherein, 'safe and effective amount' refers to: sufficient amount of compound to significantly improve disease condition without leading to serious adverse effect. Generally, pharmaceutical compositions contain 1-1000 mg of compound of the present invention per dose, preferably 5-500 mg of compound of the present invention per dose, more preferably 10-200 mg of compound of the present invention per dose.

The compounds of the present invention and pharmaceutically acceptable salts thereof can be formulated into various formulations, which comprise safe and effective amount of the compound of the present invention or pharmaceutically acceptable salts and pharmacologically acceptable excipients and carriers thereof. Wherein, 'safe and effective amount' refers to: sufficient amount of compound to significantly improve disease condition without leading to serious adverse effect. The safe and effective amount of the compound of the present invention is determined based on the specific situations such as age, disease condition, treatment course of the subject to be treated.

'Pharmaceutically acceptable excipients and carriers' refers to: one or more compatible solid or liquid fillers or gel substances, they are suitable for human use and must have enough purity and sufficiently low toxicity. 'compatibility' herein means each component in the composition and the compound of the present invention can be incorporated into each other without significantly reducing the compound's pharmaceutical effect. Part examples of pharmacologically acceptable excipients and carriers are cellulose and its derivative (eg., sodium carboxymethylcellulose, ethyl cellulose sodium, cellulose acetate, etc), gelatin, talc, solid lubricant (eg., stearic acid, magnesium stearate), calcium sulfate, vegetable oil (eg., soybean oil, sesame oil, peanut oil, olive oil, etc), polyols (eg., propylene glycol, glycerol, mannitol, sorbitol, etc), emulsifier (eg., Tween®), wetting agent (eg., sodium lauryl sulfate), colorant, flavoring agent, stabilizer, antioxidant, preservative, pyrogen-free water and so on.

The compound of the present invention, when applying, can be orally, rectally, parenterally (intravenously, intramuscularly or subcutaneously) topically administrated.

Solid dosage forms for oral administration include capsule, tablet, pill, powder and granule. Among which, active compounds are mixed with at least one common inert excipient (or carrier) such as sodium citrate or dicalcium phosphate, or mixed with the following ingredients: (a) filler or bulking agent, eg., starch, lactose, sucrose, glucose, mannitol and silicic acid; (b) binder, eg., carboxymethylcellulose, alginate, gelatin, polyvinyl pyrrolidone, sucrose and arabic gum; (c) humectant, eg., glycerol; (d) disintegrating agent, eg., agar, calcium carbonate, potato starch ortapioca starch, alginic acid, certain complex silicate, and sodium carbonate; (e) slowly dissolving agent, eg., paraffin; (f) absorption accelerator, eg., quaternary amine compound; (g) wetting agent, eg., cetanol and glyceryl monostearate; (h) adsorbent, eg., kaolin; and (i) lubricant, eg., talc, calcium stearate, magnesium stearate, solid polyethylene glycol, sodium lauryl sulfate, or mixture thereof. In capsule, tablet and pill, dosage form can also include buffer.

Solid dosage forms such as tablet, sugar pill, capsule, pill and granule can be made by coat and shell materials, eg., enteric coating and other materials well known in the art. They can comprise opacifying agent and the active compound in this composition or the release of compound can be released within a part of digestive tract in a delayed manner. Examples of the embedded components which can be used are polymeric substances and waxy substances. Active compound, when necessary, can form microcapsule with one or more of the above-mentioned excipients.

Liquid dosage forms for oral administration include pharmaceutically acceptable emulsion, solution, suspension, syrup or tincture. In addition to active compound, liquid dosage forms can include commonly employed inert diluent in the art, such as water or other solvent, solubilizer and emulsifier, eg., ethanol, isopropanol, ethyl carbonate, ethyl acetate, propylene glycol, 1,3-butanediol, dimethylformamide as well as oil, particularly cottonseed oil, peanut oil, maize embryo oil, olive oil, castor oil and sesame oil or the mixture of these substances, etc.

In addition to these inert diluents, compositions can also comprise auxiliaries, such as wetting agent, emulsifier and suspending agent, sweetener, flavoring agent and flavor.

In addition to active compound, suspension can also comprise suspending agent, such as ethoxylated isooctadecanol, polyoxyethylene sorbitan and sorbitan ester, microcrystalline cellulose, aluminium methoxide and agar or the mixture of these substances, etc.

Compositions for parenteral administration can include physiologically acceptable sterile water or nonaqueous solution, dispersion, suspension or emulsion, and sterile powders used to be redissolved into sterile injectable solution or dispersion. Suitable aqueous and nonaqueous carrier, diluent, solvent or excipient include water, ethanol, polyols and suitable mixture thereof.

The dosage forms of the compound of the present invention for topical administration include ointment, powder, patch, spray and inhalant. Active ingredients mix together with physiologically acceptable carrier and any preservative, buffer under sterile condition, or with possibly required propellant when necessary.

The compound of the present invention can be administrated alone or combined with other pharmaceutically acceptable compounds.

A safe and effective amount of the compounds of the present invention are applied to mammal (such as human) which need to be treated when using pharmaceutical composition, wherein dose is the pharmaceutically effective administration dose when applying, for a people of 60 kg body weight, daily administration dose is 1~1000 mg, preferably 10~500 mg. Of course, particular dose should consider factors such as administration route, patient health, which are within the technical scope of skilled physicians.

The major advantages of the invention include:

1. The compound of the present invention has specific effect for *Mycobacterium tuberculosi*. The compound of the present invention has superior effect for multi-drug resistant *Mycobacterium tuberculosi*.

2. The compound of the present invention has increased water-solubility. Animal drug metabolism study showed that the compound of the present invention had good pharmacokinetics characters. This has important meanings for the compound to enhance antitubercular activity, improve pharmaceutical effect, decrease side effects, reduce cost.

3. Good tissue distribution. tissue distribution study showed that the compounds of the invention mainly distributed in focus site of tubercle bacillus-lung and spleen, while distributed little in non-target tissues. The lung target indicated there would be very high the ray index and side effects would decrease significantly.

EXAMPLES

The invention will be more specifically explained in the following examples. However, it should be understood that these examples are to illustrate the invention by way of example, not to limit the scope of the invention in any way. The experimental methods which the particular condition are not illustrated in the following examples are generally performed according to common conditions, or according to the conditions recommended by manufacturer. Unless otherwise stated, parts and percent are parts by weight and percent by weight.

In the all examples, melting point is determined by X-4 Melting Point Apparatus and thermometer is uncorrected; $^1$H NMR is recorded by Varian Mercury 400 or 600 Nuclear Magnetic Resonance Spectrometer, chemical shift is expressed by δ(ppm); MS is determined by Shimadzu LC-MS-2020 Mass Spectrometer. Silica gels for isolation are all of 200-300 mesh if not specified, all eluent ratios are volume ratios.

Preparation Example 1

(4-(4-(trifluoromethoxy)phenoxy)piperidine (I-6a)

P-trifluoromethoxy phenol (32.7 g, 184 mmol), N-Boc-4-hydroxy piperidine (37 g, 184 mmol) and triphenylphosphine (48.3 g, 184 mmol) were dissolved in dry THF (500 mL), DIAD (37.2 g, 184 mmol) was added dropwise while cooling in ice-bath, followed by stirring overnight at room temperature. THF were spun out, residuals were extracted by petroleum ether, extracting solution was concentrated to give 71.2 g light yellow oily matter, crude product yield was more than 100%, directly put into the next reaction step.

The crude products obtained from the previous step (66.5 g, 184 mmol) were dissolved in TFA (500 mL), stirring at room temperature. After 3 h, TFA were spun out, add water to residuals, use NaOH solution to adjust pH to above pH 10, extract by ethyl acetate, extracting solution was concentrated followed by column chromatography to give 35.3 g white solid, yield was 73%.

ESI-LR: 262.1 [M+1]$^+$.

Preparation Example 2

4-(2-fluoro-4-(trifluoromethoxy)phenoxy)piperidine (I-6b)

Similar to the synthesis of preparation example 2, with 2-fluoro-4-(trifluoromethoxy)phenol (1.96 g, 1.0 mmol, see WO2008130581 for synthesis) and N-Boc-4-hydroxy piperidine (2.01 g, 1.0 mmol) as crude materials, 1.87 g white solid product was produced and the yield of the two steps was 67%.

ESI-LR: 280.1 [M+1]$^+$.

Preparation Example 3

4-(3-fluoro-4-(trifluoromethoxy)phenoxy)piperidine (I-6c)

Similar to the synthesis of preparation example 1, with 3-fluoro-4-(trifluoromethoxy)phenol (1.96 g, 1.0 mmol, see US2009302273 for synthesis) and N-Boc-4-hydroxy piperidine (2.01 g, 1.0 mmol) as crude materials, 2.01 g white solid product was produced and the yield of the two steps was 72%.

ESI-LR: 280.1 [M+1]$^+$.

Preparation Example 4

4-(3-chloro-4-(trifluoromethoxy)phenoxy)piperidine (I-6d)

Similar to the synthesis of preparation example 1, with 3-fluoro-4-(trifluoromethoxy)phenol (2.12 g, 1.0 mmol, see WO2008076043 for synthesis) and N-Boc-4-hydroxy piperidine (2.01 g, 1.0 mmol) as crude materials, 1.98 g white solid product was produced and the yield of the two steps was 67%.

ESI-LR: 296.1 [M+1]$^+$.

Preparation Example 5

4-(3-chloro-4-(trifluoromethyl)phenoxy)piperidine (I-6e)

Similar to the synthesis of preparation example 1, with 3-fluoro-4-(trifluoromethyl)phenol (1.96 g, 1.0 mmol, see WO2006051378 for synthesis) and N-Boc-4-hydroxy piperidine (2.01 g, 1.0 mmol) as crude materials, 1.55 g white solid product was produced and the yield of the two steps was 56%.

ESI-LR: 280.1 [M+1]$^+$.

Preparation Example 6

4-(3,5-difluoro-4-(trifluoromethoxy)phenoxy)piperidine (I-6f)

Similar to the synthesis of preparation example 1, with 3,5-difluoro-4-(trifluoromethyl)phenol (2.14 g, 1.0 mmol) and N-Boc-4-hydroxy piperidine (2.01 g, 1.0 mmol) as crude materials, gave 1.86 g white solid product, the yield of the two steps was 63%.

ESI-LR: 298.1 [M+1]$^+$.

Preparation Example 7

4-(4-(trifluoromethoxy)phenoxy)piperidine (I-6g)

(1) 4-(4-(trifluoromethoxy)phenoxy)piperidine-1-formic acid tert-butyl ester

N-Boc-4-hydroxy piperidine (2.01 g, 1.0 mmol) was dissolved in DMF (30 mL), added sodium hydride (60%, 0.6 g, 15 mmol) in ice-bath, stirred for 30 min, added p-trifluoromethoxy benzyl bromide (3.06 g, 12 mmol), after which resumed to stir for 15 h at room temperature, added ice water (30 mL) in ice-bath to quench reaction. Extracted by dichloromethane (30 mL*2), combined organic phases, the organic phases were washed by water and saturated saline respectively, dried by anhydrous sodium sulfate, concentrated column chromatography (petroleum ether: ethyl acetate=10:1) to give 2.9 g light yellow liquid, yield was 78%.

$^1$H NMR (400 MHz, CDCl$_3$): δ1.41 (s, 9H), 1.55-1.62 (m, 2H), 1.84-1.90 (m, 2H), 3.07-3.13 (m, 2H), 3.54-3.58 (m, 1H), 3.77-3.82 (m, 2H), 4.54 (s, 2H), 7.19 (d, J=7.9 Hz, 2H), 7.36 (d, J=8.6 Hz, 2H)

(2) 4-(4-(trifluoromethoxy)phenoxy)piperidine 4-(4-(trifluoromethoxy)phenoxy)piperidine-1-formic acid tert-butyl ester (2.5 g, 6.66 mmol) was dissolved in 1,4-dioxane, added dropwise hydrogen chloride in 1,4-dioxane solution, stirred for 3 h at room temperature, removed solvents after the reaction was completed, residuals were washed by petroleum ether and ethyl ether respectively to give 2.0 g white solid, yield was 99%.

ESI-LR: 276.1 [M+1]$^+$.

Preparation Example 8

3-(4-(trifluoromethoxy)phenoxy)azetidine (I-6h)

Similar to the synthesis of preparation example 2, with p-trifluoromethoxy phenol (1.78 g, 1.0 mmol) and N-Boc-3-hydroxy azetidine (1.73 g, 1.0 mmol) as crude materials, 1.38 g white solid product was produced and the yield of the two steps was 59%.

ESI-LR: 234.1 [M+1]$^+$.

Preparation Example 9

4-(4-(2,2,2-trifluoroethoxy)phenoxy)piperidine (I-6i)

4-(4-hydroxyphenyl)piperidine-1-tert-butyl carbonate (2.0 g, 6.8 mmol, see WO2006064218 for synthesis) was dissolved in dry HMPA (20 mL), added sodium hydride (326 mg, 8.4 mmol) in ice-bath, added 2,2,2-trifluoro iodoethane (1.72 mg, 8.2 mmol), increased temperature to 140° C. enclosed tube, stirred the reaction for 18 h, added water (30 mL), extracted by ethyl acetate (40 mL*2), combined organic phases, the organic phases were washed by water and saturated saline, dried by anhydrous sodium sulphate, concentrated, column chromatography (PE: EA=20:1~15:1) to give 1.0 g light yellow solid, yield was 39%.

Product 4-(4-(2,2,2-trifluoroethoxy)phenoxy)piperidine-1-tert-butyl carbonate (751 mg, 2 mmol) obtained from the previous step was dissolved in 1,4-dioxane, added dropwise hydrogen chloride in 1,4-dioxane solution, stirred for 3 h at room temperature, removed solvents after the reaction was completed, residuals were washed by petroleum ether and ethyl ether respectively to give 600 mg white solid, yield was 96%.

ESI-LR: 276.1 [M+1]$^+$.

Preparation Example 10

4-(4-(difluoromethoxy)phenoxy)piperidine (I-6j)

Similar to the synthesis of preparation example 9, with 4-(4-hydroxyphenoxy)piperidine-1-tert-butyl carbonate (1.76 g, 0.6 mmol) and freon (3 mL, excess) as crude materials, 656 mg white solid product was produced and yield was 45%.

ESI-LR: 244.1 [M+1]$^+$.

Preparation Example 11

4-(4-(2-methoxyethoxy)phenoxy)piperidine (I-6k)

Similar to the synthesis of preparation example 9, with 4-(4-hydroxyphenoxy)piperidine-1-tert-butyl carbonate (1.76 g, 0.6 mmol) and 1-bromo-2-methoxyethanol (1.66 g, 1.2 mmol) as crude materials, 632 mg white solid product was produced and yield was 42%.

ESI-LR: 252.2 [M+1]$^+$.

Preparation Example 12

4-(4-(2-ethoxyethoxy)phenoxy)piperidine (I-6l)

Similar to the synthesis of preparation example 9, with 4-(4-hydroxyphenoxy)piperidine-1-tert-butyl carbonate (1.76 g, 0.6 mmol) and 1-bromo-2-ethoxyethanol (1.82 g, 1.2 mmol) as crude materials, 612 mg white solid product was produced and yield was 38%.

ESI-LR: 266.2 [M+1]$^+$.

Preparation Example 13

4-(4-(2-(2,2,2-trifluoroethoxy)ethoxy)phenoxy)piperidine (I-6m)

Similar to the synthesis of preparation example 9, with 4-(4-hydroxyphenoxy)piperidine-1-tert-butyl carbonate (1.76 g, 0.6 mmol) and 2-(2,2,2-trifluoromethylethoxy)ethyl p-toluenesulfonate (2.68 g, 0.9 mmol, see WO2009026537 for synthesis) as crude materials, 785 mg white solid product was produced and yield was 41%.

ESI-LR: 320.1 [M+1]$^+$.

Preparation Example 14

4-(4-(isopropoxy)phenoxy)piperidine (I-6n)

Similar to the synthesis of preparation example 9, with 4-(4-hydroxyphenoxy)piperidine-1-tert-butyl carbonate (1.76 g, 0.6 mmol) and isopropyl bromide (2.20 g, 1.8 mmol) as crude materials, 516 mg white solid product was produced and yield was 36%.

ESI-LR: 236.2 [M+1]$^+$.

Preparation Example 15

4-(4-(isobutoxy)phenoxy)piperidine (I-6o)

Similar to the synthesis of preparation example 9, with 4-(4-hydroxyphenoxy)piperidine-1-tert-butyl carbonate (1.76 g, 0.6 mmol) and isobutyl bromide (2.48 g, 1.8 mmol) as crude materials, 668 mg white solid product was produced and yield was 44%.

ESI-LR: 250.2 [M+1]$^+$.

Preparation Example 16

4-(4-(2-cyclopropoxy)ethoxy)phenoxy)piperidine (I-6p)

Similar to the synthesis of preparation example 9, with 4-(4-hydroxyphenoxy)piperidine-1-tert-butyl carbonate (1.76 g, 0.6 mmol) and (2-bromoethoxy)cyclopropane (1.48 g, 0.9 mmol) as crude materials, 768 mg white solid product was produced and yield was 46%.

ESI-LR: 278.2 [M+1]$^+$.

Preparation Example 17

N-(4-trifluoromethoxy)benzylpiperazine (I-6q)

(1) N-tert-butyloxycarbonyl-N'-(4-trifluoromethoxy)benzylpiperazine

N-tert-butyloxycarbonyl piperazine (373 mg, 2 mmol), 4-trifluoromethoxy benzyl bromide (510 mg, 2 mmol) were dissolved in THF (20 mL), added NaI (50 mg), stirred for 12 h at room temperature, filtered out insolubles, filtrates were subjected to column chromatography (PE: EtoAc=5:1) after concentration to give N-tert-butyloxycarbonyl-N'-(4-trifluoromethoxy)benzylpiperazine as 519 mg colorless oily matter, yield was 72%.

$^1$H NMR (400 MHz, CDCl$_3$): δ1.43 (s, 9H), 2.35 (t, J=5.3 Hz, 4H), 3.42 (t, J=5.2 Hz, 4H), 3.49 (s, 2H), 7.15 (d, J=8.2 Hz, 2H), 7.34 (d, J=8.4 Hz, 2H)

(2) N-(4-trifluoromethoxy)benzylpiperazine

Trifluoroacetic acid (5 mL) was added to N-tert-butyloxycarbonyl-N'-(4-trifluoromethoxy)benzylpiperazine (384 mg, 1.07 mmol), stirred for 0.5 h at room temperature, trifluoroacetic acid was spun out, residuals were added to methyl tert-butyl ether (20 mL) and water (20 mL), NaOH solution was used to adjust to alkaline pH, partitioned, aqueous phase was further extracted by methyl tert-butyl ether (20 mL), combined ether phases, washed by water and saturated saline, subjected to anhydrous sodium sulfate drying, concentrated after filtering out drying agent to give 227 mg title compound, yield was 82%.

$^1$H NMR (400 MHz, CDCl$_3$): δ2.39 (s, 4H), 2.78-2.91 (m, 5H), 3.45 (s, 2H), 7.12 (d, J=8.5 Hz, 2H), 7.31 (d, J=8.7 Hz, 2H)

Preparation Example 18

N-(4-(trifluoromethoxy)phenyl)piperidine-4-amine (I-6r)

1-BOC-4-piperidineketone (4.0 g, 0.02 mol) was dissolved in dichloromethane (250 mL), at room temperature, added p-trifluoromethoxy aniline (4.3 g, 0.024 mol), added acetic acid (1.44 g, 0.024 mol), added sodium triacetoxyborohydride (8.5 g, 0.04 mol), stirred reaction for 18 h at room temperature under argon protection, TLC monitored. Added an appropriate amount of 1M NaOH after the reaction was completed, mixture was extracted by dichloromethane, combined organic phases, followed by anhydrous sodium sulphate drying, filtration, concentration, spinning dry to give 7.5 g raw solid product 4-(4-trifluoromethoxy aniline)piperidin-1-yl-formic acid tert-butyl ester, yield was 100%. Directly put into the next step.

4-(4-trifluoromethoxy aniline)piperidin-1-yl-formic acid tert-butyl ester (7.2 g, 0.02 mol) obtained from the previous step was dissolved in 1,4-dioxane (200 mL), added dropwise HCl in 1,4-dioxane solution in ice-bath, after which stirred overnight at room temperature, TLC monitored. After the reaction was finished, filtered, washed by n-hexane and ethyl ether, since hydrochloride easily absorbed water, NH3 in methanol solution made it free, to give title compound as 5.0 g white solid, yield was 96%.

$^1$H NMR (400 MHz, DMSO-$d_6$): δ1.70-1.78 (m, 2H), 2.05-2.08 (m, 2H), 2.96-3.01 (m, 2H), 3.29-3.51 (m, 2H), 5.77-5.79 (m, 1H), 6.57-6.60 (m, 2H), 6.89-6.91 (m, 2H),

Preparation Example 19

4-(4-trifluoromethoxy)phenyl)piperidine (I-6s)

(1) 4-hydroxy-4-(4-(trifluoromethoxy)phenyl)piperidine-1-formic acid tert-butyl ester 4-trifluoromethoxy bromobenzene (2.41 g, 10 mmol) was dissolved in dry tetrahydrofuran (30 mL), cooled to −78° C., to which slowly added dropwise n-butyllithium (1.6M n-hexane solution, 6.5 mL), kept the temperature below −70° C. during the dropwise adding procedure, after adding, kept stirring this system for 20 min, added 4-carbonyl piperidine-1-formic acid tert-butyl ester (1.99 g, 10 mmol) in tetrahydrofuran solution, kept the temperature below −70° C. during the dropwise adding procedure, after adding, the temperature can be increased to room temperature while stirring for 15 h. After the reaction was finished, added saturated ammonium chloride aqueous solution to quench reaction, partitioned, organic phases were washed by saturated saline, followed by anhydrous sodium sulphate drying, concentration, column chromatography (PE: EA=15:1) to give 1.6 g light yellow gel-like substance, yield: 40%.

MS (ESI/LR): 362.2 [M+1]$^+$.

(2) 4-(4-(trifluoromethoxy)phenyl)piperidine-1-formic acid tert-butyl ester 4-hydroxy-4-(4-(trifluoromethoxy)phenyl)piperidine-1-formic acid tert-butyl ester (1.85 g, 5 mmol) was dissolved in dry dichloromethane (30 mL), cooled to −20° C., added dropwise triethyl silicane (696 mg, 6 mmol), added slowly until completed, slowly resumed to stir for 15 h at room temperature. After the reaction was finished, added ice water to quench reaction, partitioned, organic phases were washed by saturated saline, followed by sodium sulphate drying, concentration, column chromatography (PE: EA=20:1) to give 0.6 g light yellow gel-like substance, yield: 34%.

MS (ESI/LR): 346.2 [M+1]$^+$.

(3) 4-(4-(trifluoromethoxy)phenyl)piperidine 4-(4-(trifluoromethoxy)phenyl)piperidine-1-formic acid tert-butyl ester (1.73 g, 5 mmol) was dissolved in methanol (15 mL), added HCl/MeOH saturated solution (15 mL), stirred for 3 h at room temperature, removed solvents under reduced pressure, residuals were washed by ethyl ether to give 1.4 g white solid, ie 4-(4-(trifluoromethoxy)phenyl)piperidine hydrochloride, yield was 100%.

MS (ESI/LR): 246.1 [M+1]$^+$.

Preparation Example 20

4-(4-trifluoromethoxy)benzyl)piperidine (I-6t)

(1) (4-(trifluoromethoxy)phenyl)methyl diethylphosphate

Triethyl phosphate (2.7 g, 15 mmol) was added to p-trifluoromethoxy benzyl bromide (2.56 g, 10 mmol), raised the temperature to 120° C. and stirred the reaction for 3 h. After the reaction was finished, column chromatography generated 2.2 g light yellow oily matter, yield: 72%.

MS (ESI/LR): 313.1 [M+1]$^+$.

(2) 4-(4-trifluoromethoxy)benzyl)piperidine-1-formic acid tert-butyl ester (4-(trifluoromethoxy)phenyl)methyl diethyl phosphate (3.1 g, 10 mmol) was dissolved in anhydrous tetrahydrofuran (50 mL), added 15-crown-15 (0.2 mol, 1 mol), in ice-bath until −5° C., to which added sodium hydride (60%, 480 mg, 12 mmol), resumed to stir for half an hour at room temperature, added 4-carbonyl piperidine-1-formic acid tert-butyl ester (1.99 g, 10 mmol) in tetrahydrofuran solution, then stirred for 18 h at room temperature, added water, solution was extracted by ethyl acetate, organic phases were dried, concentrated and subjected to column chromatography to give 1.8 g light yellow solid, yield was 51%.

The resultant solid described above was dissolved in ethanol, added 10% Pd/C (200 mg), reacted for 15 h at room temperature, filtered, filtrates were concentrated and subjected to column chromatography to give 1.2 g gel-like substance, yield was 67%.

MS (ESI/LR): 360.2 [M+1]$^+$.

(3) 4-(4-trifluoromethoxy)benzyl)piperidine 4-(4-trifluoromethoxy)phenyl)piperidine-1-formic acid tert-butyl ester (1.2 g, 3.3 mmol) was dissolved in 10 mL methanol, added HCl/MeOH saturated solution (10 mL), stirred for 3 h at room temperature, removed solvents under reduced pressure, residuals were washed by ethyl ether to give 0.96 g white solid, ie 4-(4-(trifluoromethoxy)benzyl) piperidine, yield was 97%.

MS (ESI/LR): 260.1 [M+1]$^+$.

Preparation Example 21

2-(4-(4-(trifluoromethoxy)phenoxy)piperidin-1-yl)ethanol (I-6u)

4-(4-(trifluoromethoxy)phenoxy)piperidine (1.31 g, 5.0 mmol) was dissolved in dry dichloromethane (30 mL), cooled to 0° C. in ice salt-bath, added ethylene oxide (2.55 mL, 50 mmol), reacted for 3 h in ice salt-bath, stopped the reaction, the reaction was monitored by TLC, the system was spun dry after complete reaction to give 1.52 g title compound, yield was 100%.

MS (ESI/LR): 348.2 [M+1]$^+$.

Preparation Example 22

3-(4-(4-trifluoromethoxy)phenoxy)piperidin-1-yl) propionyl chloride (II-4a)

(1) 3-(4-(4-trifluoromethoxy)phenoxy)piperidin-1-yl)ethyl propionate (II-2a)

4-(4-trifluoromethoxy)phenoxy)piperidine (2.61 g, 10 mmol) was dissolved in acetonitrile (20 mL), added potassium carbonate (2.76 g, 20 mmol) and 3-ethyl-bromopropionate (2.72 g, 15 mmol), raised the temperature to reflux for 3 h, filtered, the filtrates were concentrated, purified by column chromatography (eluent $CH_2Cl_2$: MeOH=30:1) to give 1.36 g product, yield was 38%.

$^1$H NMR (400 MHz, $CDCl_3$): δ1.29 (t, 3H), 2.02-2.05 (m, 4H), 2.45-2.70 (m, 6H), 3.71-3.75 (m, 3H), 4.33-4.38 (m, 2H), 6.88 (d, J=9.1 Hz, 2H), 7.12 (d, J=8.8 Hz, 2H)

(2) 3-(4-(4-(trifluoromethoxy)phenoxy)piperidin-1-yl)propionic acid (II-3a)

3-(4-(4-trifluoromethoxy)phenoxy)piperidin-1-yl)ethyl propionate (1.36 g, 3.78 mmol) was dissolved in THF (20 mL), cooled to 0° C., added 1N NaOH (4.5 mL) and water (4.5 mL), raised to room temperature and stirred for 3 h, organic phases were spun out, again added an appropriate amount of water, washed by ethyl acetate, partitioned out aqueous phase, pH value was adjusted to about 2.5 by concentrated hydrochloric acid, ie, there was product precipitation, filtered, vacuum dried, generated 800 mg product, yield was 64%.

$^1$H NMR (400 MHz, $CDCl_3$): δ2.02-2.05 (m, 4H), 2.45-2.70 (m, 4H), 3.71-3.75 (m, 3H), 4.33-4.38 (m, 2H), 6.88 (d, J=9.1 Hz, 2H), 7.12 (d, J=8.8 Hz, 2H).

(3) 3-(4-(4-trifluoromethoxy)phenoxy)piperidin-1-yl)propionyl chloride (II-4a)

3-(4-(4-(trifluoromethoxy)phenoxy)piperidin-1-yl) propionic acid (333 mg, 1 mmol) was dispersed in 5 mL toluene, added oxalyl chloride (0.13 mL, 1.5 mmol) and 2 drops of DMF, stirred the reaction at room temperature until no bubble released, spun dry, residuals were washed by an appropriate amount of ethyl ether to give 291 mg product, yield was 75%, directly put to the next reaction step.

Preparation Example 23

3-(3-(4-(trifluoromethoxy)phenoxy)azetidin-1-yl) propionyl chloride (II-4b)

(1)-3-(3-(4-(trifluoromethoxy)phenoxy)azetidin-1-yl)ethyl propionate (II-2b)

3-(4-(trifluoromethoxy)phenoxy)azetidine (1.17 g, 5 mmol) was dissolved in acetonitrile (20 mL), added potassium carbonate (2.76 g, 20 mmol) and 3-ethyl-bromopropionate (1.36 g, 7.5 mmol), raised the temperature to reflux for 3 h, filtered, the filtrates were concentrated, purified by column chromatography (eluent $CH_2Cl_2$: MeOH=20:1) to give target product (586 mg, 35%).

MS (ESI/LR): 334.1 $[M+1]^+$.

(2)-3-(3-(4-(trifluoromethoxy)phenoxy)azetidin-1-yl)propionic acid (II-3b)

3-(3-(4-(trifluoromethoxy)phenoxy)azetidin-1-yl)ethyl propionate (551 mg, 1.65 mmol) was dissolved in THF (8 mL), cooled to 0° C., added NaOH (80.0 mg, 2 mmol) and water (2 mL), raised to room temperature and stirred for 3 h, organic phases were spun out, again added an appropriate amount of water, adjusted to about pH2.5 by concentrated hydrochloric acid, washed once by dichloromethane, partitioned, spun dry aqueous phase, vacuum dried, generated target compound (408 mg, 81%).

$^1$H NMR (400 MHz, $CDCl_3$): δ2.78-2.91 (m, 6H), 3.45 (s, 2H), 4.54 (m, 1H), 7.12 (d, J=8.5 Hz, 2H), 7.31 (d, J=8.7 Hz, 2H).

(3) 3-(3-(4-(trifluoromethoxy)phenoxy)azetidin-1-yl)propionyl chloride (II-4b)

3-(3-(4-(trifluoromethoxy)phenoxy)azetidin-1-yl)propionic acid (400 mg, 1.31 mmol) was dissolved in thionyl chloride, raised the temperature to reflux for 3 h, spun dry, residuals were washed by an appropriate amount of ethyl ether, generated 423 mg target product, yield was 100%, directly put to the next reaction step.

Preparation Example 24

3-(4-(4-trifluoromethoxy)benzyl)piperazin-1-yl)propionyl chloride (II-4c)

(1) 3-(4-(4-trifluoromethoxy)benzyl)piperazin-1-yl)ethyl propionate (II-2c)

N-(4-trifluoromethoxy)benzyl piperazine (1.48 g, 5 mmol) was dissolved in acetonitrile (20 mL), added potassium carbonate (2.76 g, 20 mmol) and 3-ethyl-bromopropionate (1.36 g, 7.5 mmol), raised the temperature to reflux for 3 h, filtered, the filtrates were concentrated, purified by column chromatography (eluent $CH_2Cl_2$: MeOH=30:1) to give target product (610 mg, 34%).

$^1$H NMR (400 MHz, $CDCl_3$): δ1.3 (t, 3H), 2.39 (s, 4H), 2.76-2.98 (m, 9H), 3.45-3.53 (m, 2H), 4.12-4.16 (m, 2H), 7.12 (d, J=8.5 Hz, 2H), 7.31 (d, J=8.7 Hz, 2H).

(2) 3-(4-(4-trifluoromethoxy)benzyl)piperazin-1-yl) propionic acid (II-3c)

3-(4-(4-trifluoromethoxy)benzyl)piperazin-1-yl)ethyl propionate (557 mg, 1.55 mmol) was dissolved in THF (8 mL), cooled to 0° C., added NaOH (74.4 mg, 1.86 mmol) and water (2 mL), raised to room temperature and stirred for 3 h, organic phases were spun out, again added an appropriate amount of water, adjusted to about pH 2.5 by concentrated hydrochloric acid, washed once by dichloromethane, partitioned, spun dry aqueous phase, vacuum dried, generated target product (410 mg, 79%).

$^1$H NMR (400 MHz, $CDCl_3$): δ2.39 (s, 4H), 2.78-2.91 (m, 8H), 3.45 (s, 2H), 7.12 (d, J=8.5 Hz, 2H), 7.31 (d, J=8.7 Hz, 2H).

(3)-3-(4-(4-trifluoromethoxy)benzyl)piperazin-1-yl) propionyl chloride (II-4c)

3-(4-(4-trifluoromethoxy)benzyl)piperazin-1-yl)propionic acid (530 mg, 14 mmol) was dissolved in thionyl chloride, raised the temperature to reflux for 3 h, spun dry, residuals were washed by an appropriate amount of ethyl ether, generated 530 mg target product, yield was 98%, directly put to the next reaction step.

Preparation Example 25

3-(2-(4-(4-(trifluoromethoxy)phenoxy)piperidin-1-yl)ethoxy)propionyl chloride (II-4d)

(1) 3-(2-(4-(4-(trifluoromethoxy)phenoxy)piperidin-1-yl)ethoxy)ethyl propionate (II-2d)

2-(4-(4-(trifluoromethoxy)phenoxy)piperidin-1-yl)ethanol (1.22 g, 4.0 mmol) was dissolved in acetonitrile (20 mL), added potassium carbonate (2.76 g, 20 mmol) and 3-ethylbromopropionate (1.09 g, 6.0 mmol), raised the temperature to reflux for 3 h, filtered, the filtrates were concentrated, purified by column chromatography (eluent $CH_2Cl_2$: MeOH=15:1), generated target product (984 mg, 61%).
MS (ESI/LR): 405.2 $[M+1]^+$.

(2) 3-(2-(4-(4-(trifluoromethoxy)phenoxy)piperidin-1-yl)ethoxy)propionic acid (II-3d)

3-(2-(4-(4-(trifluoromethoxy)phenoxy)piperidin-1-yl)ethoxy)ethyl propionate (607 mg, 1.5 mmol) was dissolved in THF (20 mL), cooled to 0° C., added 1N NaOH (3.0 mL) and water (3.0 mL), raised to room temperature and stirred for 3 h, organic phases were spun out, again added an appropriate amount of water, washed by ethyl acetate, partitioned out aqueous phase, pH value was adjusted to about 2.5 by concentrated hydrochloric acid, then there was product precipitation, filtered, vacuum dried, generated 452 mg product, yield was 80%.
$^1$H NMR (400 MHz, $CDCl_3$): δ2.02-2.05 (m, 4H), 2.45-2.70 (m, 8H), 3.71-3.78 (m, 4H), 4.33-4.38 (m, 1H), 6.88 (d, J=9.1 Hz, 2H), 7.12 (d, J=8.8 Hz, 2H).

(3) 3-(2-(4-(4-(trifluoromethoxy)phenoxy)piperidin-1-yl)ethoxy)propionyl chloride (II-4d)

3-(2-(4-(4-(trifluoromethoxy)phenoxy)piperidin-1-yl)ethoxy)propionic acid (377 mg, 1.0 mmol) was dissolved in thionyl chloride, raised the temperature to reflux for 3 h, spun dry, residuals were washed by an appropriate amount of ethyl ether, generated 395 mg target product, yield was 100%, directly put to the next reaction step.

Preparation Example 26

4-(3-(4-(trifluoromethoxy)phenoxy)azetidin-1-yl)butyryl chloride (III-4)

(1) 4-(3-(4-(trifluoromethoxy)phenoxy)azetidin-1-yl)ethyl butyrate (III-2)

3-(4-(trifluoromethoxy)phenoxy)azetidine (1.17 g, 5 mmol) was dissolved in acetonitrile (20 mL), added potassium carbonate (2.76 g, 20 mmol) and 4-ethyl-bromobutyrate (1.46 g, 7.5 mmol), raised the temperature to reflux for 3 h, filtered, the filtrates were concentrated, purified by column chromatography (eluent $CH_2Cl_2$: MeOH=20:1), generated target product (584 mg, 33%).
MS (ESI/LR): 348.2 $[M+1]^+$.

(2) 4-(3-(4-(trifluoromethoxy)phenoxy)azetidin-1-yl)butyric acid (III-3)

4-(3-(4-(trifluoromethoxy)phenoxy)azetidin-1-yl)ethyl butyrate (572 mg, 1.65 mmol) was dissolved in THF (8 mL), cooled to 0° C., added NaOH (80.0 mg, mmol) and water (2 mL), raised to room temperature and stirred for 3 h, organic phases were spun out, again added an appropriate amount of water, pH value was adjusted to about 2.5 by concentrated hydrochloric acid, washed once by dichloromethane, partitioned, spun dry aqueous phase, vacuum dried, generated target product (433 mg, 82%).
$^1$H NMR (400 MHz, $CDCl_3$): δ1.46 (m, 2H), 2.78-2.91 (m, 6H), 3.46 (s, 2H), 4.52 (m, 1H), 7.12 (d, J=8.5 Hz, 2H), 7.31 (d, J=8.6 Hz, 2H).

(3) 4-(3-(4-(trifluoromethoxy)phenoxy)azetidin-1-yl)butyryl chloride (III-4)

4-(3-(4-(trifluoromethoxy)phenoxy)azetidin-1-yl)butyric acid (412 mg, 1.29 mmol) was dissolved in thionyl chloride, raised the temperature to reflux for 3 h, spun dry, residuals were washed by an appropriate amount of ethyl ether, generated 421 mg target product, yield was 97%, directly put to the next reaction step.

Preparation Example 27

(S)-2-chloro-N-(2-nitro-6,7-dihydro-5H-imidazo[2,1-b][1,3]oxazin-6-yl)acetamide (I-8)

Under argon protection, I-7-(S)-(2-nitro-6,7-dihydro-5H-imidazo[2,1-b][1,3]oxazine-6-amine (134 mg, 0.73 mmol) was dissolved in anhydrous DMF (2 mL), added triethylamine (0.3 mL, 2.18 mmol), added dropwise chloroacetyl chloride (0.082 mL, 1.09 mmol) at 0° C., stirred for 2 h at room temperature, added saturated sodium bicarbonate solution, extracted by ethyl acetate, followed by anhydrous sodium sulphate drying and suction filtration, spun dry solvents, separated by column chromatography to give 92 mg yellow viscous liquid, yield was 50%.
$^1$H NMR (400 MHz, $CDCl_3$): δ3.7 (s, 2H), 4.36 (dt, $J_1$=2.4 Hz, $J_2$=13.5 Hz, 1H), 4.58 (dd, $J_1$=3.6 Hz, $J_2$=13.5 Hz, 1H), 4.62-4.74 (m, 3H), 7.83 (s, 1H).

Example 1

(S)—N-(6,7-dihydro-2-nitro-5H-imidazo[2,1-b][1,3]oxazin-6-yl)-2-(4-(4-(trifluoromethoxy)phenoxy)piperidin-1-yl)acetamide (1)

Under argon protection, (S)-2-chloro-N-(2-nitro-6,7-dihydro-5H-imidazo[2,1-b][1,3]oxazin-6-yl)acetamide (130 mg, 0.50 mmol) was dissolved in anhydrous DMF (2 mL), added 4-(4-trifluoromethoxy)phenoxy)piperidine (261 mg, 1.0 mmol), potassium carbonate (207 mg, 1.5 mmol), stirred overnight at 50° C., separated by column chromatography to give title compound as 102 mg yellow powder, yield was 42%.
$^1$H NMR (400 MHz, $CDCl_3$): δ2.42-2.53 (m, 8H), 3.44 (m, 2H), 3.47 (s, 2H), 4.19-4.28 (m, 3H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 486.3 $[M+1]^+$.

Example 2

2-(4-(2-fluoro-4-(trifluoromethoxy)phenoxy)piperidin-1-yl)-N—((S)-6,7-dihydro-2-nitro-5H-imidazo[2,1-b][1,3]oxazin-6-yl)acetamide (2)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(2-fluoro-4-(trifluoromethoxy)phenoxy)piperidine (279 mg, 1.0 mmol) as crude materials, 128 mg title compound was generated and yield was 51%.

$^1$H NMR (400 MHz, CDCl$_3$): δ2.42-2.53 (m, 8H), 3.44 (m, 2H), 3.47 (s, 2H), 4.19-4.28 (m, 3H), 4.47-4.52 (m, 2H), 4.62-4.63 (m, 1H), 7.15 (d, J=15.4 Hz, 1H), 7.32-7.43 (m, 2H), 7.61 (s, 1H), 7.92 (m, 1H). ESI-LR: 504.1 [M+1]$^+$.

Example 3

2-(4-(3-fluoro-4-(trifluoromethoxy)phenoxy)piperidin-1-yl)-N—((S)-6,7-dihydro-2-nitro-5H-imidazo[2,1-b][1,3]oxazin-6-yl)acetamide (3)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(3-fluoro-4-(trifluoromethoxy)phenoxy)piperidine (279 mg, 1.0 mmol) as crude materials, 137 mg title compound was generated and yield was 55%.

$^1$H NMR (400 MHz, CDCl$_3$): δ2.42-2.53 (m, 8H), 3.44 (m, 2H), 3.47 (s, 2H), 4.19-4.28 (m, 3H), 4.47-4.52 (m, 2H), 4.62-4.63 (m, 1H), 7.15 (d, J=15.4 Hz, 1H), 7.32-7.43 (m, 2H), 7.61 (s, 1H), 7.92 (m, 1H). ESI-LR: 504.1 [M+1]$^+$.

Example 4

2-(4-(3-chloro-4-(trifluoromethoxy)phenoxy)piperidin-1-yl)-N—((S)-6,7-dihydro-2-nitro-5H-imidazo[2,1-b][1,3]oxazin-6-yl)acetamide (4)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(3-chloro-4-(trifluoromethoxy)phenoxy)piperidine (295 mg, 1.0 mmol) as crude materials, generated 98 mg title compound, yield was 38%.

$^1$H NMR (400 MHz, CDCl$_3$): δ2.42-2.53 (m, 8H), 3.44 (m, 2H), 3.47 (s, 2H), 4.19-4.28 (m, 3H), 4.47-4.52 (m, 2H), 4.62-4.63 (m, 1H), 7.15 (d, J=2.7 Hz, 1H), 7.32-7.43 (m, 2H), 7.61 (s, 1H), 7.92 (m, 1H). ESI-LR: 520.1 [M+1]$^+$.

Example 5

2-(4-(3-chloro-4-(trifluoromethyl)phenoxy)piperidin-1-yl)-N—((S)-6,7-dihydro-2-nitro-5H-imidazo[2,1-b][1,3]oxazin-6-yl)acetamide (5)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(3-chloro-4-(trifluoromethyl)phenoxy)piperidine (279 mg, 1.0 mmol) as crude materials, 162 mg title compound was generated and yield was 65%.

$^1$H NMR (400 MHz, CDCl$_3$): δ2.42-2.53 (m, 8H), 3.44 (m, 2H), 3.47 (s, 2H), 4.19-4.28 (m, 3H), 4.47-4.52 (m, 2H), 4.62-4.63 (m, 1H), 7.15 (d, J=2.7 Hz, 1H), 7.32-7.43 (m, 2H), 7.61 (s, 1H), 7.92 (m, 1H). ESI-LR: 504.1 [M+1]$^+$.

Example 6

(S)-2-(4-(3,5-difluoro-4-(trifluoromethoxy)phenoxy)piperidin-1-yl)-N-(2-nitro-6,7-dihydro-5H-imidazo[2,1-b][1,3]oxazin-6-yl)acetamide (6)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(3,5-difluoro-4-(trifluoromethoxy)phenoxy)piperidine (297 mg, 1.0 mmol) as crude materials, 87 mg title compound was generated and yield was 33%.

$^1$H NMR (400 MHz, CDCl$_3$): δ2.42-2.53 (m, 8H), 3.44 (m, 2H), 3.47 (s, 2H), 4.19-4.28 (m, 3H), 4.47-4.52 (m, 2H), 4.62-4.63 (m, 1H), 7.06 (m, 2H), 7.92 (m, 1H). ESI-LR: 522.1 [M+1]$^+$.

Example 7

(S)—N-(6,7-dihydro-2-nitro-5H-imidazo[2,1-b][1,3]oxazin-6-yl)-2-(4-(4-(trifluoromethoxy)phenoxy)piperidin-1-yl)acetamide (7)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(trifluoromethoxy)phenoxy)piperidine (275 mg, 1.0 mmol) as crude materials, title compound as 140 mg yellow powder was generated and yield was 56%.

$^1$H NMR (400 MHz, CDCl$_3$): δ2.42-2.53 (m, 8H), 3.34-3.44 (m, 2H), 3.48 (s, 2H), 4.20-4.28 (m, 3H), 4.46-4.51 (m, 2H), 4.57 (s, 2H), 4.63-4.64 (m, 1H), 7.20 (d, J=8.0 Hz, 2H), 7.38 (d, J=8.0 Hz, 2H), 7.50 (s, 1H), 7.95 (d, J=7.2 Hz, 1H). ESI-LR: 500.2 [M+1]$^+$.

Example 8

2-(3-(4-(trifluoromethoxy)phenoxy)azetidin-1-yl)-N—((S)-6,7-dihydro-2-nitro-5H-imidazo[2,1-b][1,3]oxazin-6-yl)acetamide maleate (8)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 3-(4-(trifluoromethoxy)phenoxy)azetidine (233 mg, 1.0 mmol) as crude materials, 128 mg 2-(3-(4-(trifluoromethoxy)phenoxy) azetidin-1-yl)-N—((S)-6,7-dihydro-2-nitro-5H-imidazo[2,1-b][1,3]oxazin-6-yl)acetamide was generated and yield was 56%.

2-(3-(4-(trifluoromethoxy)phenoxy)azetidin-1-yl)-N—((S)-6,7-dihydro-2-nitro-5H-imidazo[2,1-b][1,3]oxazin-6-yl)acetamide (33 mg, 0.07 mmol) was dissolved in isopropanol (2 mL), added dropwise maleic acid (8 mg, 0.08 mmol) in isopropanol solution at room temperature, after which stirred for 10 min, filtered, recrystallize to give 18 mg light yellow solid, yield was 45%.

$^1$H NMR (400 MHz, CDCl$_3$): δ3.91-4.03 (m, 5H), 4.28-4.53 (m, 7H), 6.06 (s, 2H), 6.94-6.97 (m, 2H), 7.32-7.34 (m, 2H), 8.12 (s, 1H), 8.91 (m, 1H). ESI-LR: 458.2 [M+1]$^+$.

Example 9

(S)-2-(4-(4-(2,2,2-trifluoroethoxy)phenoxy)piperidin-1-yl)-N-2-nitro-6,7-dihydro-5H-imidazo[2,1-b][1,3]oxazin-6-yl)acetamide (9)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(2,2,2-trifluoroethoxy)phenoxy)piperidine (275 mg, 1.0 mmol) as crude materials, 113 mg title compound was generated and yield was 47%.

$^1$H NMR (400 MHz, CDCl$_3$): δ2.42-2.53 (m, 8H), 3.44 (m, 2H), 3.47 (s, 2H), 4.19-4.28 (m, 3H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 486.3 [M+1]$^+$.

Example 10

(S)-2-(4-(4-(difluoromethoxy)phenoxy)piperidin-1-yl)-N-(2-nitro-6,7-dihydro-5H-imidazo[2,1-b][1,3]oxazin-6-yl)acetamide (10)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(difluoromethoxy)phenoxy)piperidine (243 mg, 1.0 mmol) as crude materials, 82 mg title compound was generated and yield was 43%.
$^1$H NMR (400 MHz, CDCl$_3$): δ2.42-2.53 (m, 8H), 3.44 (m, 2H), 4.19-4.28 (m, 3H), 4.47-4.52 (m, 2H), 4.62-4.63 (m, 1H), 4.47-4.52 (m, 2H), 7.15 (d, J=8.0 Hz, 2H), 7.32 (d, J=8.0 Hz, 2H), 7.41 (s, 1H), 7.92 (d, J=7.2 Hz, 1H). ESI-LR: 468.2 [M+1]$^+$.

Example 11

(S)-2-(4-(4-(2-methoxyethoxy)phenoxy)piperidin-1-yl)-N-(2-nitro-6,7-dihydro-5H-imidazo[2,1-b][1,3]oxazin-6-yl)acetamide (11)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(2-methoxyethoxy)phenoxy)piperidine (251 mg, 1.0 mmol) as crude materials, 134 mg title compound was generated and yield was 56%.
$^1$H NMR (400 MHz, CDCl$_3$): δ2.42-2.53 (m, 8H), 3.40 (s, 3H), 3.44 (m, 2H), 3.62-3.67 (m, 2H), 4.19-4.28 (m, 5H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 476.2 [M+1]$^+$.

Example 12

(S)-2-(4-(4-(2-ethoxyethoxy)phenoxy)piperidin-1-yl)-N-(2-nitro-6,7-dihydro-5H-imidazo[2,1-b][1,3]oxazin-6-yl)acetamide (12)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(2-ethoxyethoxy)phenoxy)piperidine (265 mg, 1.0 mmol) as crude materials, 75 mg title compound was generated and yield was 63%.
$^1$H NMR (400 MHz, CDCl$_3$): δ1.23 (t, 3H), 2.42-2.53 (m, 8H), 3.42 (q, 2H), 3.44 (m, 2H), 3.62-3.67 (m, 2H), 4.19-4.28 (m, 5H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 490.2 [M+1]$^+$.

Example 13

(S)-2-(4-(4-(2-(2,2,2-trifluoroethoxy)ethoxy)phenoxy)piperidin-1-yl)-N-(2-nitro-6,7-dihydro-5H-imidazo[2,1-b][1,3]oxazin-6-yl)acetamide (13)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(2-(2,2,2-trifluoroethoxy)ethoxy)phenoxy)piperidine (319 mg, 1.0 mmol) as crude materials, 75 mg title compound was generated and yield was 27%.
$^1$H NMR (400 MHz, CDCl$_3$): δ2.42-2.53 (m, 8H), 3.44 (m, 2H), 3.49 (s, 2H), 3.62-3.67 (m, 2H), 4.19-4.28 (m, 5H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 544.2 [M+1]$^+$.

Example 14

(S)-2-(4-(4-isopropoxy)phenoxy)piperidin-1-yl)-N-(2-nitro-6,7-dihydro-5H-imidazo[2,1-b][1,3]oxazin-6-yl)acetamide (14)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-isopropoxy)phenoxy)piperidine (235 mg, 1.0 mmol) as crude materials, 89 mg title compound was generated and yield was 39%.
$^1$H NMR (400 MHz, CDCl$_3$): δ1.10 (m, 6H), 1.23-1.31 (m, 1H), 2.42-2.53 (m, 8H), 3.44 (m, 2H), 3.62-3.67 (m, 2H), 4.23-4.34 (m, 4H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 460.2 [M+1]$^+$.

Example 15

(S)-2-(4-(4-isobutoxy)phenoxy)piperidin-1-yl)-N-(2-nitro-6,7-dihydro-5H-imidazo[2,1-b][1,3]oxazin-6-yl)acetamide (15)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-isobutoxy)phenoxy)piperidine (249 mg, 1.0 mmol) as crude materials, generated 103 mg title compound, yield was 42%.
$^1$H NMR (400 MHz, CDCl$_3$): δ1.10 (d, 6H), 1.23-1.31 (m, 1H), 2.42-2.53 (m, 8H), 3.44 (m, 2H), 3.62-3.67 (m, 2H), 4.23-4.34 (m, 4H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 474.2 [M+1]$^+$.

Example 16

(S)-2-(4-(4-(2-(cyclopropoxy)ethoxy)phenoxy)piperidin-1-yl)-N-(2-nitro-6,7-dihydro-5H-imidazo[2,1-b][1,3]oxazin-6-yl)acetamide (16)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(2-(cyclopropoxy)ethoxy)phenoxy)piperidine (277 mg, 1.0 mmol) as crude materials, 97 mg title compound was generated and yield was 39%.
$^1$H NMR (400 MHz, CDCl$_3$): δ0.45 (m, 2H), 0.67 (m, 2H), 2.42-2.53 (m, 8H), 3.42 (q, 2H), 3.44 (dd, J=19.6 Hz, 2H), 3.62-3.67 (m, 2H), 4.19-4.28 (m, 4H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). M+1: 502.2;

Example 17

(S)—N-6,7-dihydro-2-nitro-5H-imidazo[2,1-b][1,3]oxazin-6-yl)-2-(4-(4-(trifluoromethoxy)benzyl)piperazin-1-yl)acetamide (17)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and N-(4-trifluoromethoxy)benzylpiperazine (260 mg, 1.0 mmol) as crude materials, 157 mg title compound was generated and yield was 65%.

$^1$H NMR (400 MHz, CDCl$_3$): δ2.42-2.53 (m, 8H), 3.44 (dd, J$_1$=19.6 Hz, J$_2$=16.4 Hz, 2H), 3.47 (s, 2H), 4.19-4.28 (m, 2H), 4.47-4.52 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 485.3 [M+1]$^+$.

Example 18

(S)—N-2-nitro-6,7-dihydro-5H-imidazo[2,1-b][1,3]oxazin-6-yl)-2-(4-(4-(trifluoromethoxy)phenylamino)piperidin-1-yl)acetamide (18)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and N-(4-(trifluoromethoxy)phenyl)piperidine-4-amine (260 mg, 1.0 mmol) as crude materials, 63 mg title compound was generated and yield was 26%.

$^1$H NMR (400 MHz, CDCl$_3$): δ1.90-2.07 (m, 2H), 2.27-2.35 (m, 2H), 2.60-2.95 (m, 4H), 3.06 (d, J=2.4 Hz, 2H), 3.32-3.36 (m, 1H), 4.24-4.25 (m, 2H), 4.51-4.60 (m, 2H), 4.62-4.64 (m, 1H), 6.52 (d, J=12.0 Hz, 1H), 7.01 (d, J=12.0 Hz, 2H), 7.43 (s, 1H), 7.94 (d, J=8.8 Hz, 1H). ESI-LR: 485.2 [M+1]$^+$.

Example 19

N—((S)-6,7-dihydro-2-nitro-5H-imidazo[2,1-b][1,3]oxazin-6-yl)-2-(4-(4-(trifluoromethoxy)phenyl)piperidin-1-yl)acetamide Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(trifluoromethoxy)phenyl)piperidine (245 mg, 1.0 mmol) as crude materials, 140 mg title compound was generated and yield was 60%.

$^1$H NMR (400 MHz, CDCl$_3$): δ2.38-2.50 (m, 8H), 2.78 (m, 1H), 3.45 (dd, J$_1$=19.6 Hz, J$_2$=16.4 Hz, 2H), 4.19-4.27 (m, 2H), 4.46-4.53 (m, 2H), 4.62-4.63 (m, 1H), 7.16 (d, J=8.0 Hz, 2H), 7.35 (d, J=7.8 Hz, 2H), 7.45 (s, 1H), 7.95 (d, J=7.1 Hz, 1H). ESI-LR: 470.2 [M+1]$^+$.

Example 20

2-(4-(4-(trifluoromethoxy)benzyl)piperidin-1-yl-N—((S)-6,7-dihydro-2-nitro-5H-imidazo[2,1-b][1,3]oxazin-6-yl)-acetamide Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 4-(4-(trifluoromethoxy)benzyl)piperidine (259 mg, 1.0 mmol) as crude materials, 150 mg title compound was generated and yield was 62%.

$^1$H NMR (400 MHz, CDCl$_3$): δ1.9-1.98 (m, 1H), 2.40-2.51 (m, 8H), 3.25 (s, 2H), 3.43 (dd, J$_1$=19.6 Hz, J$_2$=16.4 Hz, 2H), 4.18-4.26 (m, 2H), 4.45-4.51 (m, 2H), 4.62-4.63 (m, 1H), 7.15 (d, J=8.0 Hz, 2H), 7.32 (d, J=8.0 Hz, 2H), 7.41 (s, 1H), 7.92 (d, J=7.2 Hz, 1H). ESI-LR: 484.2 [M+1]$^+$.

Example 21

2-(2-(4-(4-(trifluoromethoxy)phenoxy)piperidin-1-yl)ethoxy)-N—((S)-6,7-dihydro-2-nitro-5H-imidazo[2,1-b][1,3]oxazin-6-yl)acetamide (21)

Similar to the manipulation of example 1, with (S)-2-chloro-N-(2-nitro-6,7-dihydro-5H-imidazo[2,1-b][1,3]oxazin-6-yl)acetamide (130 mg, 0.50 mmol) and 2-(4-(4-(trifluoromethoxy)phenoxy)piperidin-1-yl)ethanol (305 mg, 1.0 mmol) as crude materials, 125 mg title compound was generated and yield was 47%.

$^1$H NMR (400 MHz, CDCl$_3$): δ2.39 (m, 4H), 2.78-2.91 (m, 6H), 3.94-3.99 (m, 2H), 4.16-4.42 (m, 3H), 7.12 (d, J=8.5 Hz, 2H), 7.31 (d, J=8.7 Hz, 2H), 7.52 (s, 1H).
ESI-LR: 530.2 [M+1]$^+$.

Example 22

(S)—N-(6,7-dihydro-2-nitro-5H-imidazo[2,1-b][1,3]oxazin-6-yl)-3-(4-(4-(trifluoromethoxy)phenoxy)piperidin-1-yl) propanamide (22)

Under Ar, (S)-(2-nitro-6,7-dihydro-5H-imidazo[2,1-b][1,3]oxazine-6-amine (110 mg, 0.6 mmol) was dissolved in DMF (6 mL), cooled to 0° C., added Et$_3$N (0.21 mL, 2 mmol), added 3-(4-(4-(trifluoromethoxy)phenoxy)piperidin-1-yl) propionyl chloride (291 mg, 0.75 mmol) in batches, naturally rose to room temperature and stirred for 3 h, added an appropriate amount of dichloromethane, washed by distilled water for 3 times, followed by anhydrous sodium sulphate drying, filtrated out drying agent and spinning dry, residuals were purified by column chromatography (eluent CH$_2$Cl$_2$:MeOH=30:1) to give 70 mg target product, yield was 23%.

$^1$H NMR (400 MHz, CDCl$_3$): δ2.39 (s, 4H), 2.78-2.91 (m, 9H), 3.94-3.99 (m, 2H), 4.16-4.42 (m, 3H), 7.12 (d, J=8.5 Hz, 2H), 7.31 (d, J=8.7 Hz, 2H), 7.52 (s, 1H). ESI-LR: 500.2 [M+1]$^+$.

Example 23

3-(3-(4-(trifluoromethoxy)phenoxy)azetidin-1-yl)-N—((S)-6,7-dihydro-2-nitro-5H-imidazo[2,1-b][1,3]oxazin-6-yl) propanamide (23)

Similar to the manipulation of example 22, with (S)-(2-nitro-6,7-dihydro-5H-imidazo[2,1-b][1,3]oxazine-6-amine (110 mg, 0.6 mmol) and 3-(3-(4-(trifluoromethoxy)phenoxy)azetidin-1-yl) propionyl chloride (242 mg, 0.72 mmol) as crude materials, title compound as 91 mg yellow powder was generated and yield was 32%.

$^1$H NMR (400 MHz, CDCl$_3$): δ2.47 (m, 2H), 3.23-3.28 (m, 4H), 3.77-3.80 (m, 1H), 3.99-3.92 (m, 1H), 4.16-4.29 (m, 2H), 4.46-4.55 (m, 2H), 4.65-4.67 (m, 1H), 4.73-4.76 (m, 1H), 6.69-7.72 (m, 2H), 7.11-7.13 (m, 2H), 7.40 (s, 1H), 7.79 (d, 1H, J=7.8 Hz). ESI-LR: 472.1 [M+1]$^+$.

Example 24

(S)—N-(6,7-dihydro-2-nitro-5H-imidazo[2,1-b][1,3]oxazin-6-yl)-3-(4-(4-(trifluoromethoxy)benzyl)piperazin-1-yl) propanamide (24)

Similar to the manipulation of example 22, with (S)-(2-nitro-6,7-dihydro-5H-imidazo[2,1-b][1,3]oxazine-6-amine (110 mg, 0.6 mmol) and 3-(4-(4-(trifluoromethoxy)benzyl) piperazin-1-yl)) propionyl chloride (278 mg, 0.72 mmol) as crude materials, title compound as 93 mg yellow powder was generated and yield was 31%.

$^1$H NMR (400 MHz, CDCl$_3$): δ2.39 (s, 4H), 2.78-2.91 (m, 8H), 3.45 (s, 2H), 3.94-3.99 (m, 2H), 4.16-4.42 (m, 3H), 7.12 (d, J=8.5 Hz, 2H), 7.31 (d, J=8.7 Hz, 2H), 7.52 (s, 1H). ESI-LR: 499.2 [M+1]$^+$.

Example 25

3-(2-(4-(4-(trifluoromethoxy)phenoxy)piperidin-1-yl)ethoxy)-N—((S)-6,7-dihydro-2-nitro-5H-imidazo[2,1-b][1,3]oxazin-6-yl) propanamide (25)

Similar to the manipulation of example 22, with (S)-(2-nitro-6,7-dihydro-5H-imidazo[2,1-b][1,3]oxazine-6-amine (110 mg, 0.6 mmol) and 3-(2-(4-(4-(trifluoromethoxy)phenoxy)piperidin-1-yl)ethoxy) propionyl chloride (296 mg, 0.72 mmol) as crude materials, title compound as 124 mg yellow powder was generated and yield was 38%.

$^1$H NMR (400 MHz, CDCl$_3$): δ2.32-2.38 (m, 4H), 2.54 (m, 2H), 2.78-2.91 (m, 6H), 3.94-3.99 (m, 2H), 4.16-4.42 (m, 3H), 7.12 (d, J=8.5 Hz, 2H), 7.31 (d, J=8.7 Hz, 2H), 7.52 (s, 1H). ESI-LR: 543.2 [M+1]$^+$.

Example 26

4-(3-(4-(trifluoromethoxy)phenoxy)azetidin-1-yl)-N—((S)-6,7-dihydro-2-nitro-5H-imidazo[2,1-b][1,3]oxazin-6-yl)butyrylamide (26)

Similar to the manipulation of example 22, with (S)-(2-nitro-6,7-dihydro-5H-imidazo[2,1-b][1,3]oxazine-6-amine (110 mg, 0.6 mmol) and 4-(3-(4-(trifluoromethoxy)phenoxy) azetidin-1-yl)ethoxy) butyryl chloride (253 mg, 0.72 mmol) as crude materials, title compound as 108 mg yellow powder was generated and yield was 37%.

$^1$H NMR (400 MHz, CDCl$_3$): δ1.48 (m, 2H), 2.47 (m, 2H), 3.23-3.28 (m, 4H), 3.77-3.80 (m, 1H), 3.99-3.92 (m, 1H), 4.16-4.29 (m, 2H), 4.46-4.55 (m, 2H), 4.65-4.67 (m, 1H), 4.73-4.76 (m, 1H), 6.69-7.72 (m, 2H), 7.11-1.13 (m, 2H), 7.40 (s, 1H), 7.79 (d, 1H, J=7.8 Hz). ESI-LR: 486.2 [M+1]$^+$.

various compound produced in examples 1-26 are designated as compound 1-compound 26 respectively (table 1).

Example 27

Activity Test for *Mycobacterium tuberculosis*

Tested *Mycobacterium tuberculosis* strain H37Rv was transferred to liquid medium, cultured for 2 weeks at 37° C., drew a little culture liquid of bacterium and placed into 4 mL liquid medium, added 10~20 sterile glass bead of 2~3 diameter, shook for 20~30S, absolute-rest precipitated for 10~20 min, aspirated bacterium suspension supernatant, turbidity was adjusted to 1 Maxwell unit with liquid medium, equivalent to 1×10$^7$CFU/mL for use. Each drug was dissolved to 1 mg/mL by adding an appropriate amount of DMSO, filtered through 0.22 μm filter. Again diluted to the required experimental concentration with liquid medium. The final concentration of test drugs were set as follows: 0.001 μg/mL, 0.002 μg/mL, 0.004 μg/mL, 0.008 μg/mL, 0.015 μg/mL, 0.03 μg/mL, 0.06 μg/mL, 0.12 μg/mL, 0.25 μg/mL, 0.5 μg/mL, 1 μg/mL, 2 μg/mL, 4 μg/mL, 8 μg/mL and 16 μg/mL, there totally are 15 concentration gradients. 100 μL of each above-mentioned drug solution was added to 96-well microplate, further added 100 μL 1 mg/mL bacteria liquid so that drug concentration could reach the set final concentration, cultured at 37° C. The same drug dilution was done in triplicate in parallel, control group didn't added drug, inoculation amount was set to 100%, 10% and 1% respectively. Minimal inhibitory concentration (MIC) for *Mycobacterium tuberculosis* by each drug was observed, and compared with MIC results of first-line antituberculosis drug ethambutol and PA-824 in clinical research phase at the same time. The results are shown in the table below.

| Test compound | Minimal inhibitory concentration for H37Rv (μg/mL) |
|---|---|
| 1 | 0.03 |
| 3 | 0.06 |
| 9 | 0.06 |
| 14 | 0.06 |
| 16 | 0.03 |
| 17 | 0.12 |
| 22 | 0.06 |
| 26 | 0.03 |
| ethambutol | 0.5 |
| PA-824 | 0.12 |

In vitro screening results for H37Rv showed that, compound 1, compound 16 and compound 26 exhibited equally strong antitubercular activity, their minimal inhibitory concentration (MIC) for H37Rv are 16 times as that of ethambutol, and also their activity are 4 times as that of PA-824 in clinical research phase. Compound 3, compound 9, compound 14 and compound 22 exhibited equally strong activity, their MIC values are 8 times as that of ethambutol, 2 times as that of PA-824. The results showed that the compound of the invention had much higher antitubercular activity than the first-line antituberculotics ethambutol, and also had stronger antitubercular activity than PA-824 which was going on sale soon.

Example 28

Test for Drug-Resistance *Mycobacterium Buberculosis*

Test strains (246: resistant to streptomycin; 242: resistant to isoniazide; 261: resistant to rifampicin. All of them are WHO QC baterium) were transferred to liquid medium, cultured for 2 weeks at 37° C., drew a little culture liquid of bacterium and placed into 4 mL liquid medium, added 10~20 sterile glass bead of 2~3 diameter, shook for 20~30 s, absolute-rest precipitated for 10~20 min, aspirated bacterium suspension supernatant, turbidity was adjusted to 1 Maxwell unit by liquid medium, equivalent to 1×10$^7$CFU/mL for use. Each drug was dissolved to 1 mg/mL by adding an appropriate amount of DMSO, filtered through 0.22 μm filter. Again diluted to the required experimental concentration with liquid medium. The final concentration of test drugs were set as follows: 0.03125 μg/mL, 0.0625 m/mL, 0.125 μg/mL, 0.25 μg/mL, 0.5 μg/mL, 1 μg/mL, 2 μg/mL, 4 μg/mL, 8 μg/mL and 16 μg/mL, there totally are 10 concentration gradients. 100 μL of each above-mentioned drug solution was added to 96-well microplate, further added 100 μL 1 mg/mL bacteria liquid so that drug concentration could reach the set final concentration, cultured at 37° C. The same drug dilution was done in triplicate in parallel and control group didn't add any drug, inoculation amount was set to 100%, 10% and 1% respectively. Minimal inhibitory concentration (MIC) for *Mycobacterium tuberculosis* by each drug was observed, and compared with MIC results of PA-824 at the same time. The results are shown in the table below.

| | drug-resistance bacteria | | |
|---|---|---|---|
| | MIC (ug/mL) | | |
| Compound No. | 246 (S mono-resistance) | 242 (H mono-resistance) | 261 (R mono-resistance) |
| 1 | <0.03125 | 0.5 | <0.03125 |
| 22 | 0.0625 | 0.5 | <0.03125 |
| PA-824 (control) | 0.5 | 1 | 0.5 |

S: streptomycin, H: isoniazide, R: rifampicin

From the test results of above table, both compound 1 and compound 22 have very strong anti-bacterium activity for drug resistance *Mycobacterium tuberculosi*, eg., their MIC values are 16 times and 8 times as that of PA-824 for streptomycin resistance 246, 2 times and 2 times as that of PA-824 for isoniazide resistance 242, 16 times and 16 times as that of PA-824 for rifampicin resistance 261.

Example 29

Test for Water-Solubility 3-5 mg tested compound was added to 0.5 mL pH=1.2 HCL aqueous solution, shook for 3 days in a shaker, samples were centrifuged at 10000 r/min for 5 min, aspirated 2 mL supernatant to 50 mL volumetric flask, added water and metered volume to the mark to make sample solution; precisely weighted 2.6 mg sample to 50 mL volumetric flask, added an appropriate amount of methanol to dissolve. Added water and metered volume to the mark, shook up to give control sample solution. Loaded 20 μL sample solution and control sample solution respectively, tested for liquid phase. Calculated as follows:

Solubility (mg/mL)=$C$(control)*25*$A$(sample)/$A$(control)

C(control): the concentration of control sample
A(sample): peak area of liquid phase of sample solution
A(control): peak area of liquid phase of control sample solution

| Test compound No. | Solubility |
|---|---|
| 1 | 0.7464 mg/mL |
| 17 | 1.4582 mg/mL |
| 22 | 0.6774 mg/mL |
| 26 | 0.8457 mg/mL |
| PA-824(control) | 0.0094 mg/mL |

All compounds of the invention have good water-solubility, compound 17 has best water-solubility, which is 155 times as that of PA-824, the water-solubility of compound 1, compound 22 and compound 26 increase 79 times, 72 times and 90 times more than that of PA-824. Good water-solubility can improve pharmacokinetics character of drugs while promoting the production of pharmaceutic preparation.

Example 30

Drug Metabolism and Tissue Distribution Test 16 healthy male ICR mice with 18-22 g of body weight were used. Drugs were employed by intravenous or gavage administration, administration doses were 5 mg and 25 mg/kg, administration volume was 10 mL/kg. Fasted for 12 h before test with free access to water. Uniformly fed at 2 h after administration. 0.3 mL blood was drawn through mice post-glomus venous plexus according to set time points, placed in heparinized test tube, centrifuged at 3000 r/min for 10 min, separated plasma, frozen in refrigerator at −20° C. When detected, samples were treated according to plasma sample treatment method, drug concentration in plasma was determined by LC-MS method, and calculated its pharmacokinetic parameters.

pharmacokinetics parameters of compound 1 in mic

| pharmacokinetic parameters | IV (5 mg/kg) | PO (25 mg/kg) |
|---|---|---|
| $C_{max}$ (ng/mL) | 3877 | 4790 |
| $T_{max}$ (hr) | NA | 1.0 |
| $T_{1/2}$ (hr) | 2.8 | 2.7 |
| $AUC_{0-t}$ (ng * hr/L) | 7848 | 40095 |
| $AUC_{0-\infty}$ (ng * hr/L) | 7864 | 40168 |
| $MRT_{0-t}$ (hr) | 3.6 | 5.0 |
| CLz (L/hr/kg) | 0.64 | NA |
| Vz (L/kg) | 2.3 | NA |
| F (%) | | 102.18 |

NA: not applicable

Compound 1 was absorbed well by oral administration, bioavailability reached to 102.18%, good oral bioavailability has important meanings in improving pharmaceutical effect, decreasing dose and reducing cost etc.

After compound 1 was orally administrated to mice (25 mg/kg), the concentrations of the compound in embryo, lung, brain and plasma at different time was shown as FIG. 1. The result suggested that compound 1 had good tissue distribution property. Tissue distribution test showed that major distribution was in focus site of tubercle bacillus-lung and spleen, while drugs were distributed little in non-target tissues. The lung target indicated there would be very high theray index and side effects would decrease significantly.

Example 31

Pharmaceutical Composition

| Compound 1 | 20 g |
|---|---|
| Starch | 140 g |
| microcrystalline cellulose | 60 g |

According to traditional method, various ingredients of pharmaceutical composition described above, after mixing, were loaded into conventional gelatine capsule to give 1000 capsules.

According to similar method, the capsules of compound 22 were produced respectively.

Example 32

Capsule Preparation

| Compound 1 | 50 g |
|---|---|
| Starch | 400 g |
| microcrystalline cellulose | 200 g |

According to conventional method, various ingredients of pharmaceutical composition described above, after mixing, were loaded into conventional gelatine capsule to give 1000 capsules.

According to similar method, the capsules of compound 22 were produced respectively.

All the references mentioned in the invention are incorporated herein by reference, as if each reference was individually incorporated herein by reference. In addition, it should be understood that various changes or modifications can be made to the invention by those skill in the art after reading foregoing teaching, these equivalents also fall within the scope defined by the appended claims.

We claimed:

1. A compound according to formula (I) or optical isomers, pharmaceutically acceptable salts, hydrates or solvates thereof;

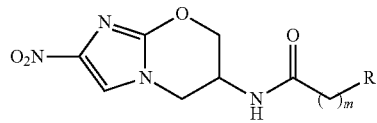

(I)

wherein, m refers to an integer between 1 and 4, R represents the following groups:

a). groups of the following structural formula

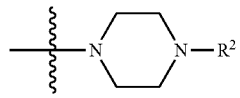

wherein, $R^2$ represents aryl methylene, which is unsubstituted or substituted by one to three groups independently selected from the following groups: halogen, halogen-substituted or unsubstituted $C_1$-$C_6$ alkoxy, halogen-substituted or unsubstituted $C_3$-$C_7$ cycloalkylalkoxy, wherein the above-mentioned alkoxy groups are selected from the following alkoxy groups: $OCH_3$, $OCF_3$, $CHF_2O$, $CF_3CH_2O$, iso-PrO, PrO, iso-BuO, cyclo-PrO, BuO, or tert-BuO;

b). groups of the following structural formula

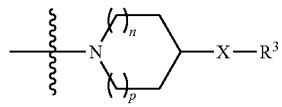

wherein, n and p represents an integer between 0 and 2 respectively, X refers to O, NH, $OCH_2$, $CH_2$ or chemical bonds, $R^3$ represents aryl, which is unsubstituted or substituted by one to three groups independently selected from the following groups: halogen, halogen-substituted or unsubstituted $C_1$-$C_6$ alkyl, halogen-substituted or unsubstituted $C_1$-$C_6$ alkoxy, halogen-substituted or unsubstituted $C_3$-$C_7$ cycloalkylalkoxy, halogen-substituted alkoxy alkoxy, wherein the above-mentioned alkoxy groups are selected from the following alkoxy groups: $OCH_3$, $OCF_3$, $CHF_2O$, $CF_3CH_2O$, $MeOCHF_2CH_2O$, $C_2H_5OCH_2CH_2O$, $CF_3CH_2OCH_2CH_2O$, iso-PrO, PrO, iso-BuO, cyclo-PrO, BuO, or tert-BuO; or c). groups of the following structural formula

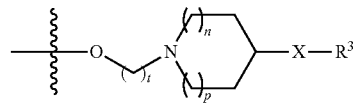

wherein, t refers to an integer between 2 and 5, n, p, X and $R^3$ are described as above.

2. The compound of claim 1, wherein, $R^2$ represents substituted or unsubstituted benzyl; $R^3$ represents substituted or unsubstituted phenyl.

3. The compound of claim 1, wherein, said $R^2$ is selected from: p-trifluoromethoxybenzyl, p-methylbenzyl, 4-(isopropoxy)benzyl or 4-(difluoromethoxy)benzyl.

4. The compound of claim 1, wherein, said $R^3$ is selected from: p-trifluoromethoxyphenyl, 2-fluoro-4-(trifluoromethoxy)phenyl, 3-fluoro-4-(trifluoromethoxy)phenyl, 3-fluoro-4-(trifluoromethoxy)phenyl, 3-fluoro-4-(trifluoromethyl)phenyl, 3,5-difluoro-4-(trifluoromethoxy)phenyl, 4-(2,2,2-trifluoroethoxy)phenyl, 4-(difluoromethoxy)phenyl, 4-(2-methoxyethoxy)phenyl, 4-(2-ethoxyethoxy)phenyl, 4-(2-(2,2,2-trifluoroethoxy)ethoxy)phenyl, 4-isopropoxyphenyl, 4-isobutoxyphenyl or 4-(2-(cyclopropoxy)ethoxy)phenyl.

5. A pharmaceutical composition comprising pharmaceutically acceptable excipients or carriers and the compound according to claim 1, or optical isomers, and pharmaceutically acceptable salts, hydrates or solvates thereof as the active ingredient.

6. The pharmaceutical composition of claim 5, wherein, said composition is in oral dosage form.

7. A method to produce a compound according to formula I-a, wherein, said method comprises the step of:

(a) Reacting a compound I-8 with a compound of formula II-b to produce the compound of formula I-a under an inert polar aprotic solvent and alkaline condition,

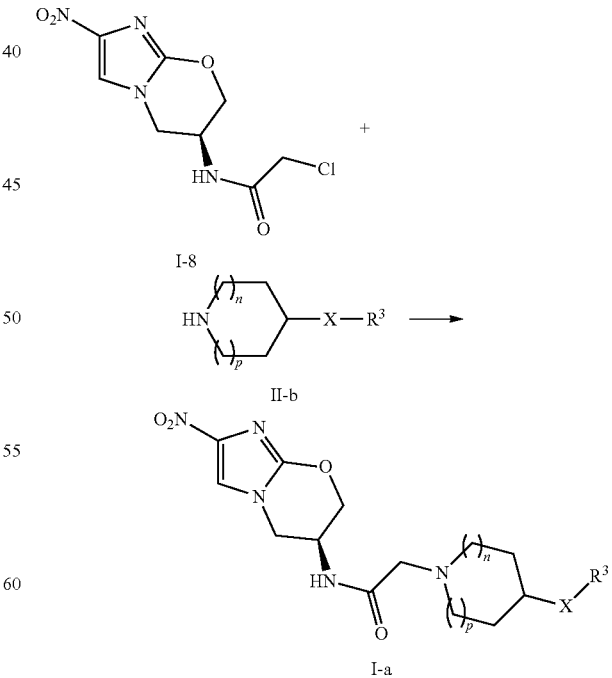

wherein, n and p represents an integer between 0 and 2 respectively,

X refers to O, NH, $OCH_2$, $CH_2$ or chemical bonds, $R^3$ represents aryl, which is unsubstituted or substituted by one to three groups independently selected from the following groups: halogen, halogen-substituted or unsubstituted $C_1$-$C_6$ alkyl, halogen substituted or unsubstituted $C_1$-$C_6$ alkoxy, halogen-substituted or unsubstituted $C_3$-$C_7$ cycloalkylalkoxy, halogen-substituted or unsubstituted alkoxyalkoxy, wherein the alkoxy groups are selected from: $OCH_3$, $OCF_3$, $CHF_2O$, $CF_3CH_2O$, $MeOCH_2CH_2O$, $C_2H_5OCH_2CH_2O$, $CF_3CH_2OCH_2CH_2O$, iso-PrO, PrO, iso-BuO, cyclo-PrO, BuO, or tert-BuO.

8. A method of suppressing the growth of *Mycobacterium tuberculosis* comprising:
administering a pharmaceutically acceptable composition to a patient, said pharmaceutical acceptable composition containing the compound according to claim 1.

9. A method of treating a patient suffering from a pulmonary tuberculosis infection comprising:
administering to the patient a composition containing the compound according to claim 1.

* * * * *